United States Patent
Doraiswamy

(10) Patent No.: US 12,083,044 B2
(45) Date of Patent: Sep. 10, 2024

(54) EYE STENTS AND DELIVERY SYSTEMS

(71) Applicant: Aquea Health, Inc., San Francisco, CA (US)

(72) Inventor: Anand Doraiswamy, Oakland, CA (US)

(73) Assignee: AQUEA HEALTH, INC., San Francisco, CA (US)

( * ) Notice: Subject to any disclaimer, the term of this patent is extended or adjusted under 35 U.S.C. 154(b) by 0 days.

(21) Appl. No.: 18/473,203

(22) Filed: Sep. 22, 2023

(65) Prior Publication Data

US 2024/0009029 A1 Jan. 11, 2024

Related U.S. Application Data

(63) Continuation of application No. 17/569,329, filed on Jan. 5, 2022, which is a continuation-in-part of (Continued)

(51) Int. Cl.
*A61F 9/007* (2006.01)

(52) U.S. Cl.
CPC .. *A61F 9/00781* (2013.01); *A61F 2210/0014* (2013.01); *A61F 2250/0067* (2013.01)

(58) Field of Classification Search
CPC .......... A61F 8/00781; A61F 2210/0014; A61F 2250/0067
See application file for complete search history.

(56) References Cited

U.S. PATENT DOCUMENTS 5,180,362 A 1/1993 Worst
5,733,329 A 3/1998 Wallace et al.
(Continued)

FOREIGN PATENT DOCUMENTS

CN 115212029 A 10/2022
EP 0898947 A2 3/1999
(Continued)

OTHER PUBLICATIONS

Co-pending U.S. Appl. No. 17/569,329, inventor Anand; Doraiswamy, filed Jan. 5, 2022.
(Continued)

*Primary Examiner* — Leslie R Deak
(74) *Attorney, Agent, or Firm* — Wilson Sonsini Goodrich & Rosati

(57) ABSTRACT

Some embodiments of the invention advantageously leverage the expansion, dilation or by-pass of the Schlemm's canal using adjustable reversible self-expanding eye stents (SES) or eye tension rings (ETRs) of desired sizes to control and improve aqueous flow throughout the range of the uveolymphatic canal. As such, some embodiments include tension ring(s) or cylinders that sits either inside or outside the Schlemm's canal wall and is at least partially within the canal and/or is partially or fully anchored, attached, adhered, or otherwise held in place with respect to the wall and/or elsewhere in the canal. The partial or complete expansion of the canal can be pre-configured based on pre-operative metrology of the Schlemm's canal to a customized and adjustable fit across the various zones within the uveolymphatic canal and based on the patient specific and evolving needs. Additionally, the SES can utilize entry/exit features for by-pass of fluid, varying control of dilation across its shape that may also allow anchoring, repositioning, and retrieval.

33 Claims, 27 Drawing Sheets

Related U.S. Application Data application No. PCT/US2020/041704, filed on Jul. 10, 2020.

(60) Provisional application No. 62/872,494, filed on Jul. 10, 2019, provisional application No. 62/874,946, filed on Jul. 16, 2019, provisional application No. 62/945,160, filed on Dec. 8, 2019.

(56) References Cited

U.S. PATENT DOCUMENTS

| | | |
|---|---|---|
| 6,214,042 B1 | 4/2001 | Jacobsen et al. |
| 6,254,592 B1 | 7/2001 | Samson et al. |
| 6,375,642 B1 | 4/2002 | Grieshaber et al. |
| 6,464,724 B1 | 10/2002 | Lynch et al. |
| 6,524,275 B1 | 2/2003 | Lynch et al. |
| 6,626,858 B2 | 9/2003 | Lynch et al. |
| 7,412,993 B2 | 8/2008 | Tzeng |
| 7,740,604 B2 | 6/2010 | Schieber et al. |
| 7,850,637 B2 | 12/2010 | Lynch et al. |
| 7,857,782 B2 | 12/2010 | Tu et al. |
| 7,909,789 B2 * | 3/2011 | Badawi ............... A61F 9/00781 604/9 |
| 8,034,105 B2 | 10/2011 | Stegmann et al. |
| 8,267,882 B2 | 9/2012 | Euteneuer et al. |
| 8,282,592 B2 | 10/2012 | Schieber et al. |
| 8,337,509 B2 | 12/2012 | Schieber et al. |
| 8,372,026 B2 | 2/2013 | Schieber et al. |
| 8,414,518 B2 | 4/2013 | Schieber et al. |
| 8,425,449 B2 | 4/2013 | Wardle et al. |
| 8,439,972 B2 | 5/2013 | Badawi et al. |
| 8,512,404 B2 | 8/2013 | Frion et al. |
| 8,529,494 B2 | 9/2013 | Euteneuer et al. |
| 8,540,659 B2 | 9/2013 | Berlin |
| 8,545,430 B2 * | 10/2013 | Silvestrini ........... A61F 9/00781 604/8 |
| 8,551,166 B2 | 10/2013 | Schieber et al. |
| 8,617,139 B2 | 12/2013 | Silvestrini et al. |
| 8,657,776 B2 | 2/2014 | Wardle et al. |
| 8,663,150 B2 | 3/2014 | Wardle et al. |
| 8,734,377 B2 | 5/2014 | Schieber et al. |
| 8,808,222 B2 | 8/2014 | Schieber et al. |
| 8,961,447 B2 | 2/2015 | Schieber et al. |
| 9,039,650 B2 | 5/2015 | Schieber et al. |
| 9,050,169 B2 | 6/2015 | Schieber et al. |
| 9,066,750 B2 | 6/2015 | Wardle et al. |
| 9,066,783 B2 | 6/2015 | Euteneuer et al. |
| 9,155,655 B2 | 10/2015 | Schieber et al. |
| 9,211,213 B2 | 12/2015 | Wardle et al. |
| 9,226,852 B2 | 1/2016 | Schieber et al. |
| 9,351,874 B2 | 5/2016 | Schieber et al. |
| 9,358,156 B2 | 6/2016 | Wardle et al. |
| 9,402,767 B2 | 8/2016 | Schieber et al. |
| 9,480,598 B2 * | 11/2016 | Clauson ............... A61F 9/00781 |
| 9,579,234 B2 | 2/2017 | Wardle et al. |
| 9,610,196 B2 | 4/2017 | Schieber et al. |
| 9,693,902 B2 | 7/2017 | Euteneuer et al. |
| 9,827,143 B2 | 11/2017 | Lynch et al. |
| 9,833,357 B2 | 12/2017 | Berlin |
| 9,931,243 B2 | 4/2018 | Wardle et al. |
| 10,154,924 B2 | 12/2018 | Clauson et al. |
| 10,537,474 B2 | 1/2020 | Euteneuer et al. |
| 10,617,558 B2 | 4/2020 | Schieber et al. |
| 11,026,836 B2 | 6/2021 | Wardle et al. |
| 11,135,088 B2 | 10/2021 | Wardle et al. |
| 11,446,179 B2 | 9/2022 | Chu |
| 2002/0077693 A1 | 6/2002 | Barclay et al. |
| 2004/0193262 A1 | 9/2004 | Shadduck |
| 2004/0254520 A1 | 12/2004 | Porteous et al. |
| 2007/0088432 A1 * | 4/2007 | Solovay ............... A61F 9/00781 623/4.1 |
| 2009/0210045 A1 | 8/2009 | Sørensen et al. |
| 2009/0287136 A1 | 11/2009 | Castillejos |
| 2011/0046728 A1 | 2/2011 | Shareef et al. |
| 2012/0010702 A1 | 1/2012 | Stegmann et al. |
| 2013/0331760 A1 * | 12/2013 | Grieshaber ......... A61F 9/00781 604/8 |
| 2014/0066821 A1 | 3/2014 | Friedland et al. |
| 2014/0081195 A1 | 3/2014 | Clauson et al. |
| 2016/0220417 A1 * | 8/2016 | Schieber ............. A61F 9/00781 |
| 2016/0287438 A1 | 10/2016 | Badawi et al. |
| 2020/0038243 A1 | 2/2020 | Badawi et al. |
| 2023/0210693 A1 | 7/2023 | Trauthen |

FOREIGN PATENT DOCUMENTS

| | | |
|---|---|---|
| EP | 2215996 A2 | 8/2010 |
| KR | 20190009569 A | 1/2019 |
| RU | 2021794 C1 | 10/1994 |
| RU | 130840 U1 | 8/2013 |
| WO | WO-0049973 A2 | 8/2000 |
| WO | WO-2021007559 A1 | 1/2021 |

OTHER PUBLICATIONS

EP20837679.8 Extended European Search Report dated Jul. 17, 2023.

PCT/US2020/041704 International Search Report and Written Opinion of the International Searching Authority dated Oct. 8, 2020.

Yan et al., Schlemm's Canal and Trabecular Meshwork in Eyes with Primary Open Angle Glaucoma: A Comparative Study Using High-Frequency Ultrasound Biomicroscopy, PLoS ONE 11(1): e0145824, Published: Jan. 4, 2016.

Kumar et al. A novel stainless steel spiral intracanalicular device for Schlemm's canal dilation to treat open-angle glaucoma. 2016. 7 pages.

U.S. Appl. No. 17/569,329 Third Party Submission Under Rule 37 CFR 1.290 dated Jan. 17, 2024.

* cited by examiner

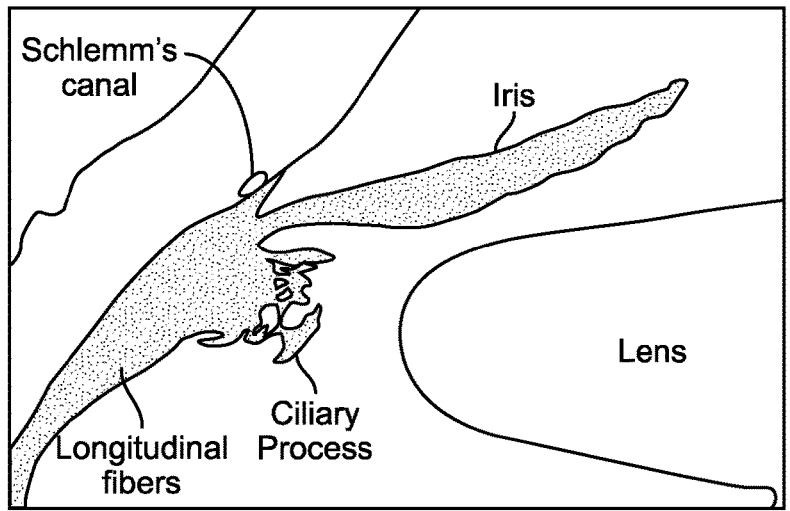
FIG. 3A
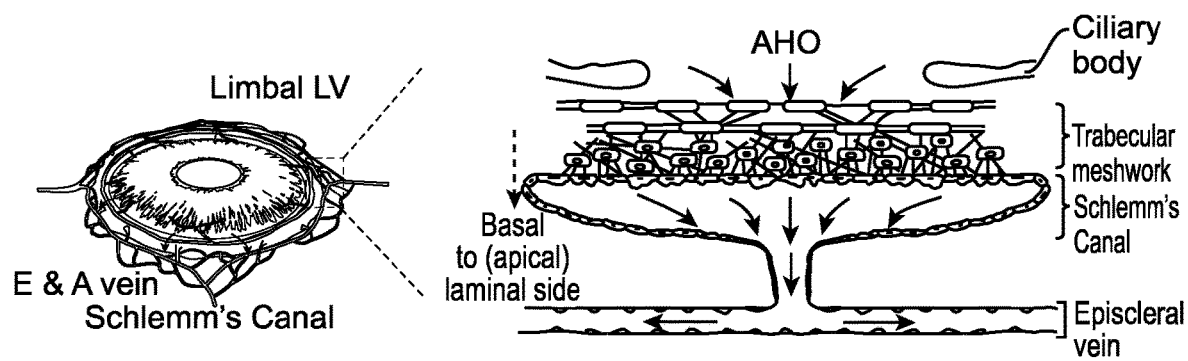
FIG. 3B
FIG. 3C
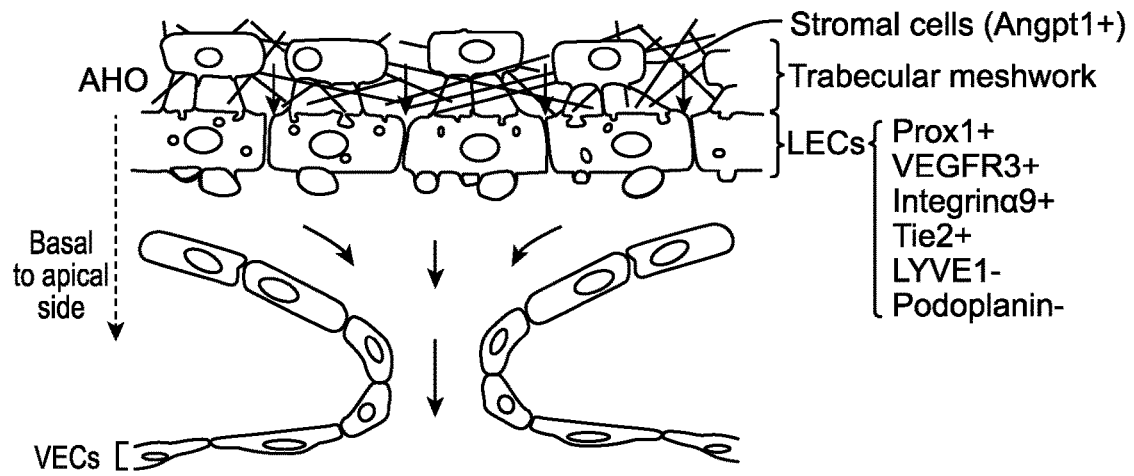
FIG. 3D

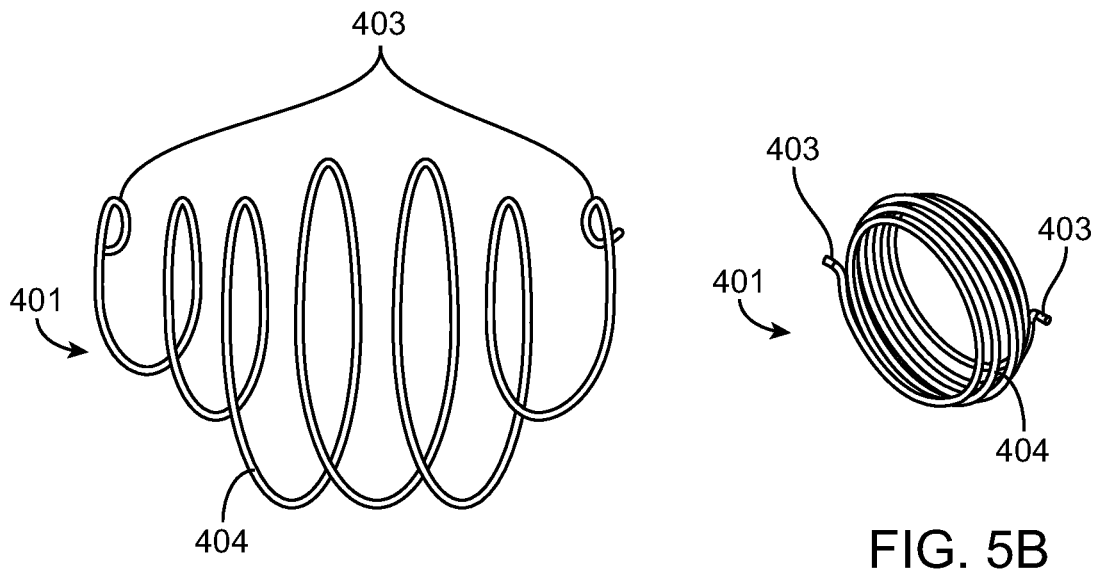
FIG. 5A
FIG. 5B
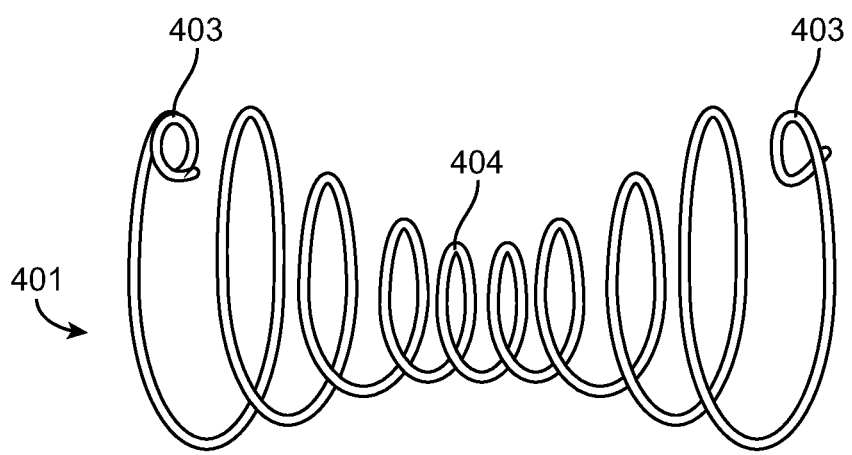
FIG. 5C

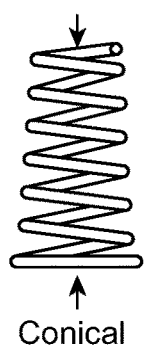
FIG. 11A
Conical
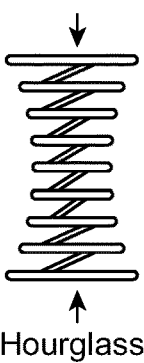
FIG. 11B
Hourglass
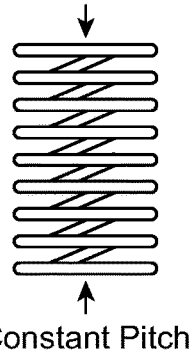
Constant Pitch
FIG. 11C
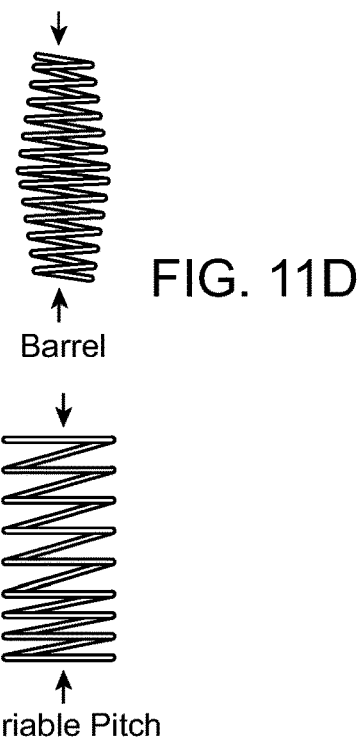
FIG. 11D
Barrel
Variable Pitch
FIG. 11E
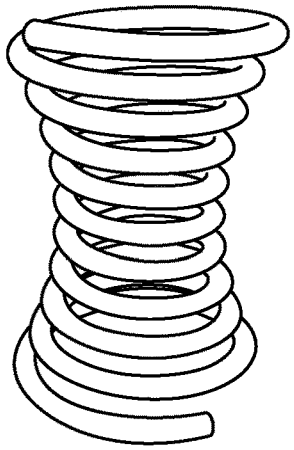
FIG. 11F
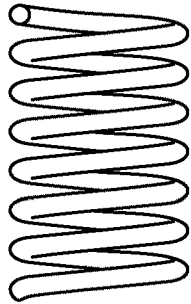
FIG. 11H
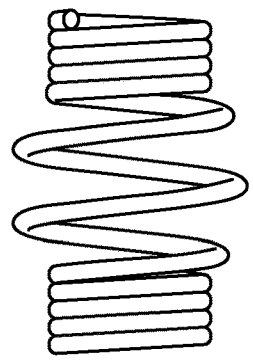
FIG. 11J
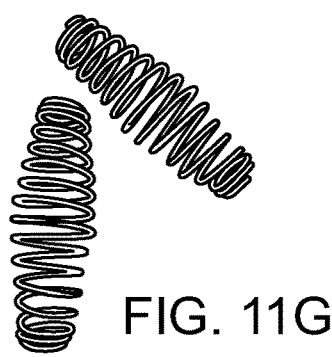
FIG. 11G
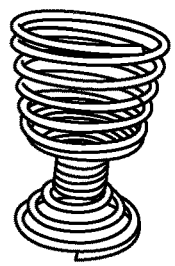
FIG. 11I

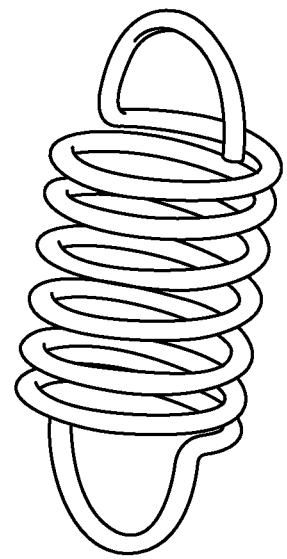
FIG. 12
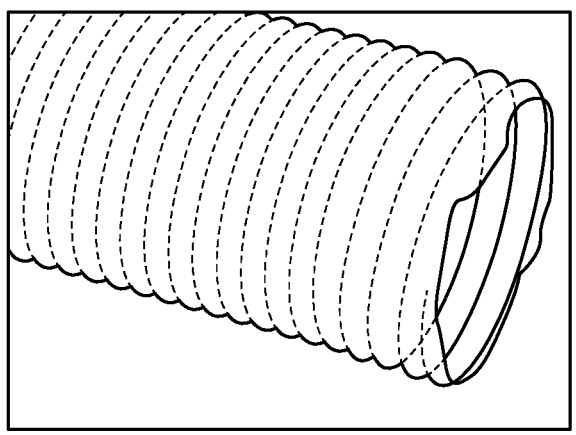          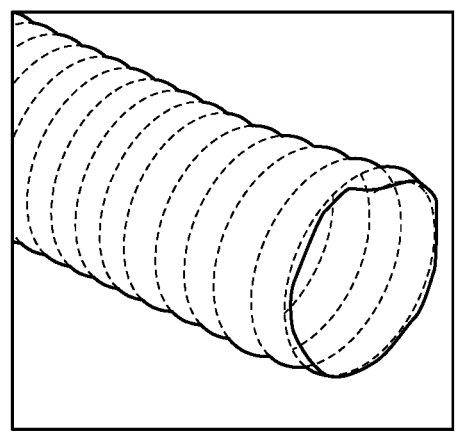
FIG. 13A          FIG. 13B

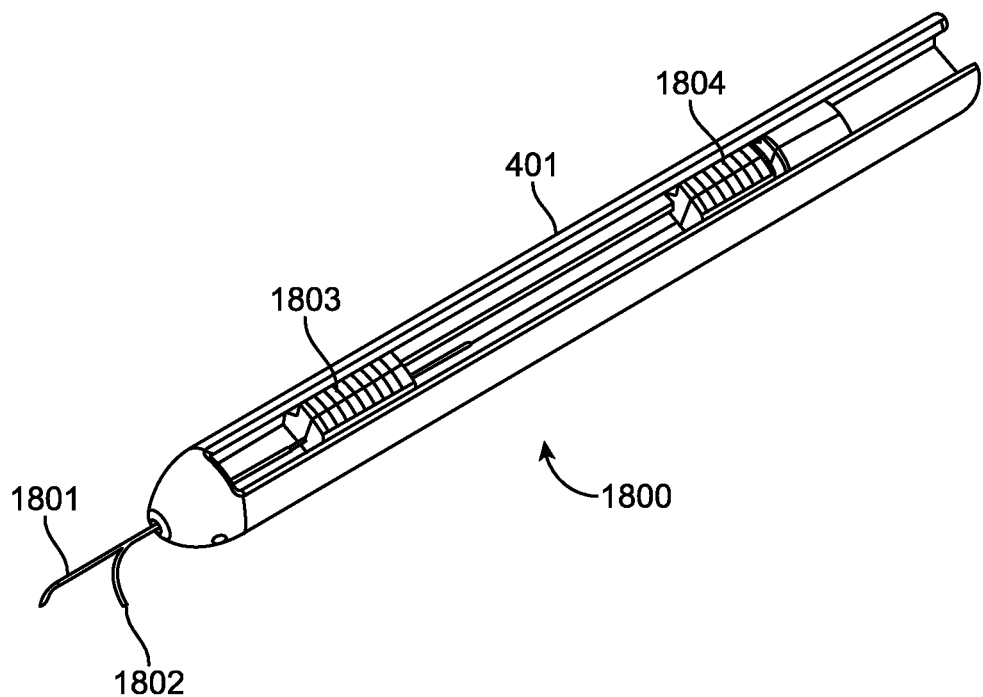
FIG. 18A
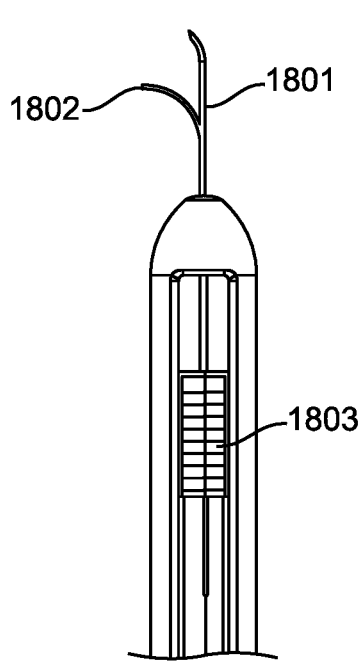 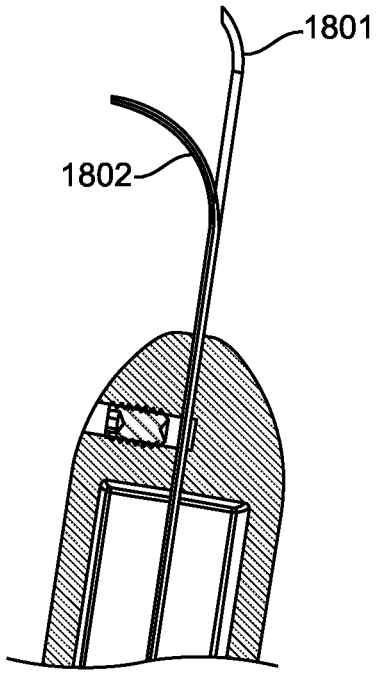
FIG. 18B  FIG. 18C

EYE STENTS AND DELIVERY SYSTEMS

CROSS-REFERENCE TO RELATED APPLICATIONS

This application is a continuation of U.S. patent application Ser. No. 17/569,329, filed Jan. 5, 2022, which is a continuation-in-part of PCT/US2020/041704, filed Jul. 10, 2020, which claims the benefit of U.S. Provisional No. 62/872,494, filed Jul. 10, 2019; U.S. Provisional No. 62/874,946, filed Jul. 16, 2019; and U.S. Provisional No. 62/945,160, filed Dec. 8, 2019, the entire contents of which are incorporated herein by reference.

BACKGROUND OF THE INVENTION

Glaucoma is the second leading cause of blindness in the world and every year, several millions of Americans lose their sight to this disabling and degenerative disease. Glaucoma is a condition that results from the elevated intraocular pressure due to various factors that irreversibly damage the eye's optic nerve. Glaucoma tends to be inherited and may not have any symptoms leading to the signs. It is estimated that there are approximately 2-3 million patients in the US who have open-angle glaucoma, a rate of ~1.9% for the US population age 40 and older.

Lowering intraocular pressure (IOP) has been the gold-standard to treating glaucoma for over a century. However, very little progress has been made in understanding how the aqueous clearance work in the eye. Recent discoveries in lymphology have shown that the Schlemm's canal is essentially a lymphatic vessel that is key in managing outflow and regulating the IOP. Lymphedema is a condition that results from the impaired flow of the lymphatics, and Glaucoma is akin to lymphedema of the eye'. Similar to other forms of lymphedema, swelling and elevated pressure is a common side-effect from the build-up of fluid with inadequate clearance.

The standard treatments of glaucoma include IOP-lowering drops, trabeculectomy, or other forms of surgical drainage devices that funnel fluid into various locations (ab-interno vs. ab-externo). Moderate and severe glaucoma are often treated with combination approaches of surgical devices and eye-drops. However, ineffective location of devices, ineffective outflow and poor compliance with eye-drops makes it difficult to address disease progression, especially since glaucoma is an asymptomatic disease.

Pharmacologic approaches for treatment include use of prostaglandin (PG) monotherapy with single agents, carbonic anhydrase inhibitors, prostaglandin analogues, beta-blockers, alpha-2 agonists, etc. Pharmacologic approaches are inadequate in the effectiveness and often used as short-term treatments. Compliance remains a large constraint for long-term effectiveness and prevention of progress. Additionally, side-effects of pharmacologic approach include brow ache, pupil constriction, burning, and reduced night vision.

Conventional and recent surgical therapies include selective laser trabeculoplasty (SLT) and microinvasive glaucoma surgery (MIGS). SLT is irreversible and requires ablation of the trabecular meshwork to create outflow networks. MIGS include a variety of devices that offer a flow channel for the aqueous fluid outside the eye (ab-externo) or inside the eye (alp-inferno). Ab-interno devices typically reside in the trabecular meshwork and ab-externo devices typically are trans/sub-conjunctival placement.

BRIEF SUMMARY OF THE INVENTION

In a first aspect, the present invention provides a device for maintaining patency of a channel of a uveolymphatic region in the eye or of the Schlemm's canal, referred to interchangeably as a channel, comprising an expansion member consisting of a single elongated element having a bent configuration for radial expansion or support of the uveolymphatic region in the eye or the Schlemm's canal. By "radial expansion or support," it is meant that a cross-section or lumen of the channel of the uveolymphatic region or the Schlemm's canal is held open and available for fluid communication with collector channels surrounding the uveolymphatic region or the Schlemm's canal to permit or enhance drainage flow from the channel of the uveolymphatic region or the Schlemm's canal into the collector channels. The expansion member in its bent configuration has (i) sufficient radial strength to withstand compressive stresses exerted by uveolymphatic region in the eye or the Schlemm's canal and (ii) sufficient void space in its structure to minimize blockage of collector channels in the uveolymphatic region in the eye or the Schlemm's canal, when the expansion member is implanted in the uveolymphatic region in the eye or the Schlemm's canal. While the expansion member may optionally be expanded in situ within the channel, as described below, usually the expansion member will be introduced into the channel in a fully expanded form and open or support the walls of the channel as it is advanced forwardly into the channel.

In an exemplary embodiment, a flexible monofilament or single-stranded helical element, usually a metal wire, such as a nickel-titanium alloy, is formed into a bent, typically helical, geometry with sufficient cross-sectional radial strength ("hoop" strength or crush resistance) to open and/or support the walls of the channel to allow unveolymphatic fluid flow within Schlemm's canal, and sufficient longitudinal flexibility to conform to a peripheral or arcuate radius of Schlemm's canal. The single-stranded helical member may comprise a closed distal loop, coil or the like to permit easy insertion and tracking within the canal, a flexible open pitch intermediate section to permit conformance to and tenting of the canal along the natural arc of the canal, and a tightly pitched or partially opened pitch at a proximal end to permit a porting effect.

While the expansion member will usually "consist of" a single-stranded or other elongated element from other structure, the device may comprise additional elements and features, such as structures located, coupled, or attached at either or both ends of the single elongated expansion member for assisting in manipulation or anchoring of the device in the uveolymphatic region and/or in the Schlemm's canal. Such features may comprise, for example, tubular, helical or other structures located at a proximal end of the single elongated element and configured to extend across the channel into the anterior chamber to create by-pass for fluid flow. In preferred instances, such features disposed at either of both ends on a single-stranded device will be formed from the single strand itself, e.g., by varying the pitch of a helical filament.

In particular embodiments, the single elongated elements of the devices of the present invention may comprise a pre-shaped metal or polymeric filament or "monofilament," where monofilament is defined as a single strand of metal or polymer. While such elongated elements, will typically comprise or consist of a single-stranded, solid core elongated wire, strand, fiber, or the like, in some instances the elongated elements might comprise a thread, cord, cable, or the like comprising multiple individual strands which are sufficiently tightly wound or otherwise bound together to act as a single solid entity. In specific examples, the single elongated strand or filament may comprise a pre-shaped metal wire, such as a shape or heat memory alloy wire. In specific examples, the single elongated element comprises a nickel-titanium alloy wire. Exemplary nickel-titanium and other metal wire devices may be formed by drawing the wire into a desired diameter and subsequently heat treating or otherwise forming the wire into a desired helical or other geometry.

The bent configuration of the single elongated element may comprise any one or combination of curves, loops, twists, turns, corners, kinks, arcs, or other non-linearities along an axial length of the single elongated elements that define a volume-occupying virtual envelope that radially supports a wall region of the uveolymphatic region in the eye or the Schlemm's canal when implanted therein. This virtual envelope will typically be generally cylindrical but could have other shapes as well. In specific examples, the single elongated element its bent configuration is at least partially formed with repeating helical turns. In other examples, the single elongated element in its bent configuration is at least partially formed with repeating serpentine loops.

In specific instances, the single elongated element may be curved along its length in its bent configuration when free from constraint, preferably conforming to a shape of the uveolymphatic region in the eye or the Schlemm's canal. In other instances, the at least one end of the single elongated element may have a geometry different than that of the remainder of the single elongated element, often having both ends with a geometry different than that of a central region of the single elongated element. The geometries at the ends may differ in only dimensions, e.g. being helical with a different wire diameter, helical diameter, and/or pitch or may differ in shape, e.g. being loops terminating either or both ends of the single elongated element.

Exemplary and preferred dimensions for shape memory helical wire embodiments of the single elongated element in its bent configuration are set forth in Table I.

TABLE I

|  | Broad Range (mm) | Medium Range (mm) | Preferred Range (mm) |
| --- | --- | --- | --- |
| Wire Diameter | 0.0001 to 1 | 0.01 to 0.15 | 0.05 to 0.1 |
| Helical Pitch (Distance between successive turns of the helix measured at midpoints of each turn) | 0.0001 to 10 | 0.1 to 2 | 0.15 to 1 |
| Helical Diameter (Measured at across outside of helical region of bent wire structure) | 0.0001 to 10 | 0.05 to 1 | 0.2 to 0.4 |

In further specific instances, at least one end of the single elongated element is formed into or otherwise comprises a tubular structure or member, such as a helix having a tighter pitch and smaller diameter than those of the central region. Often both ends of the single elongated element will be formed into a helix having a tighter pitch and smaller diameter than those of the central region, wherein tighter pitch is typically in a range from 0.001 mm to 1 mm, usually from mm to 0.2 mm, and preferably from 0.05 mm to 0.15 mm, and the smaller diameter is in a range from 0.001 mm to 1 mm, usually from 0.05 mm to 0.4 mm, and preferably from 0.1 mm to 0.3 mm.

In further embodiments of the device for maintaining patency of the present invention, the single elongated element may comprise any one or more of a variety of features, such as a radius of curvature selected to match that of the radius of curvature of the uveolymphatic canal or the Schlemm's canal of the eye. The single elongated element will also typically be polished via mechanical, chemical or electrochemical methods to improve finish and biocompatibility. The single elongated element may at least one end formed in a loop. The single elongated element may have at least one end formed as a tightly wound coil. The single elongated element may comprise at least one feature at at least one end thereof configured to facilitate manipulation. The single elongated element may be at least partially biodegradable or bioresorbable. The single elongated element may comprise a drug-eluting member formed on a surface thereof or embedded therein. The single elongated element may comprise of hydrophilic or hydrophobic coating to aid in the safety and efficacy of the device within the eye. The single elongated element may include a by-pass feature configured to permit aqueous flow between Schlemm's canal and an anterior chamber of the eye, where the by-pass feature may locate at an entry, an exit, or along a length of the device.

In a second aspect, the present invention provides method of treating glaucoma in a patient. The method typically comprises implanting an expansion member consisting of a single elongated element in an uveolymphatic channel or a Schlemm's canal of the patient. The single elongated element, when implanted, opens the uveolymphatic channel or the Schlemm's canal of the patient with (i) sufficient radial strength to withstand compressive stresses exerted by uveolymphatic region in the eye or the Schlemm's canal and (ii) sufficient void space in its structure to minimize blockage of collector channels in the uveolymphatic region in the eye or the Schlemm's canal, when the expansion member is implanted in the uveolymphatic region in the eye or the Schlemm's canal.

In specific examples of these methods of treating glaucoma of the present invention, the single elongated element typically has a bent configuration when implanted, where the term bent has been defined previously. Alternatively, the methods may further comprise introducing a delivery tube into the uveolymphatic channel or a Schlemm's canal of the patient and releasing the expansion member from constraint so that the single elongated element radially expands in situ. In either case, the single elongated element typically comprises a pre-shaped metal or polymeric filament but could also comprise any of the filaments described above.

In preferred aspects of the methods of the present invention, the single elongated element in its bent configuration is at least partially formed with repeating helical turns or with the single elongated element in its bent configuration is at least partially formed with repeating serpentine loops. Usually, the single elongated element is curved along its length in its bent configuration when free from constraint to conform to the shape of the uveolymphatic region in the eye or the Schlemm's canal. Often, the at least one end of the single elongated element has a geometry different than that of the remainder of the single elongated element, and frequently both ends of the single elongated element have a geometry different than that of a central region of the single elongated element.

In further instances of the methods herein, the radius of curvature of the single elongated element matches that of the radius of curvature of the uveolymphatic canal or the Schlemm's canal of the eye. The radius of curvature of the single elongated element may be selected to cause an inward or outward bowing of the uveolymphatic canal or the Schlemm's canal of the eye. An end of the single elongated element may be positioned to collapse Schlemm's canal to allow flow between Schlemm's canal and the trabecular meshwork.

The methods herein may further comprise additional aspects, such as eluting a drug from the single elongated element. The single elongated element may comprise a hydrophilic or hydrophobic coating to aid in the safety and efficacy of the device within the eye. The single elongated element may be positioned into an anterior chamber to provide aqueous flow at an entry, an exit, along a length of the device, into or out of the canal, or to or from the anterior chamber of the eye. The single elongated element may be implanted using fluorescence or image-guided surgery to avoid blockage of collector channels within the uveolymphatic canal or the Schlemm's canal of the eye. The single elongated element may be implanted with aid from expandable member comprising of balloon or aspiration.

Yet further specific aspects of the methods herein include customizing the single elongated element based on a pre-operative intraocular pressure IOP and desired regulation or decrease in intraocular pressure (IOP). The single elongated element may be able to deliver energy to transform the shape of the device or that of the nearby tissue.

The methods herein further comprise a variety of deliver options. The single elongated element may be delivered with a tool comprising a device channel comprising an outer sheath and an inner member, the device configured to be disposed between the inner member and the outer sheath, the delivery tool comprising a locking member configured to reversibly lock the device within the device channel. The single elongated element may be delivered with access from the angle inside the anterior chamber, or outside the eye from the sub-conjunctival region or the limbus region or the scleral region of the eye. The single elongated element may be delivered with assist from dying or visualization to access the canal of the eye in a minimally invasive manner. The single elongated element may be delivered with a delivery tool that has a pressured system to control the delivery of the device into the eye. The single elongated element may be delivered with a delivery tool that is assisted with a visualization scope or imaging. The single elongated element may be delivered with a delivery tool is attached to a syringe. The single elongated element may be delivered with a delivery tool that has a temperature control to manipulate the physical state of the device before, during and after delivery. The single elongated element may be delivered with a delivery tool that incorporates sliders or plungers or may be controlled using torsional or axial contact boards or contact rollers. The single elongated element may be delivered with a delivery tool that can also provide the incision required to enter the uveolymphatic vessel or canal. The single elongated element may be delivered with a delivery tool that can provide an expansion channel to reduce friction in delivery the device. The single elongated element may be delivered with a delivery tool that pre-tighten or wind-up the device. The single elongated element may be delivered with a delivery tool that may be powered by a piezo-electric or vibrational motor. The single elongated element may be delivered with a delivery tool that may utilize a use a guidewire to deliver, position, re-position or retract the device.

In some embodiments, the single elongated element may at least partially comprise a polymeric material selected from a group consisting of polyvinylidene fluoride, polyvinylidene difluoride (PVDF), polyvinylpyrrolidone (PVP), polyurethane, polyethylene glycol (PEG), polylactic acid (PLA), polycaprolactone (PCL), polyglycolic acid (PGA), polymethylmethacrylate (PMMA), polyacrylates, polyamide, polyimide, polyesters, silicone, carbon-composites, and the like. Such materials may be used in substantially pure form or as mixtures or composites with other materials.

In some embodiments, the single elongated element may at least partially comprise at least one metal or alloy selected from a group consisting of titanium, stainless steel, cobalt-chrome alloy, gold, platinum, silver, iridium, tantalum, tungsten, aluminum, vanadium, and the like.

Some embodiments of the invention are directed to minimally invasive systems and methods for treating glaucoma, by utilizing one, two, or more adjustable shape memory canal tension rings (or stents) configured to be placed within the canal of the uveolymphatic vessel or the Schlemm's canal. The tension ring(s) exert a radially outward mechanical force on the canal to restore the patency of the canal and improve aqueous flow therethrough, typically although not exclusively in a non-penetrating fashion. The rings can include a proximal end, distal end, and a coiled section comprising a plurality of revolutions therebetween, and proximal and distal eyelets for ease in manipulation, relocation, or retraction using a separate insertion or retrieving device. The coiled section has a variable outer diameter along its length. The rings can be made of a small diameter shape memory wire or tube (e.g., about 5-30 µm wire diameter and 150-500 µm device outer diameter), such as shape-memory alloy (SMAs), flexible metals such as stainless steel, titanium, etc. and flexible polymers including shape memory polymers (SMPs), silicone, polyvinylidene fluoride (PVDF), polymethylmethacrylate (PMMA), polypropylene (PP), polyethersulfone (PES), poly-lactic acid (PLA), poly-glycolic acid (PGA), and tunable biodegradable polymers, drug-eluting, shape memory alloys (nitinol, etc.).

Some embodiments of the invention advantageously leverage the expansion of the uveolymphatic vessel or the Schlemm's canal using adjustable and reversible self-expanding eye stents (SESs) or eye tension rings (ETRs) in the eye of desired sizes to control and improve flow throughout the range of the canal. As such, some embodiments include an adjustable tension ring(s) or cylinders that sits at least partially within the canal and/or is partially or fully anchored, attached, adhered, or otherwise held in place with respect to the canal opening or other locations within the canal and/or elsewhere in the uvea. The expansion of the canal can be configured to change at the various zones within the Schlemm's canal independently and based on the patient specific needs. In some embodiments, the tension rings may be 1, 2, 3, 4, 5, 6 separate rings of various sizes. In some embodiments, the system can be configured to control the flow rate of aqueous through the canal. In some embodiments, the rings can be substituted by cylinders, including some with fixation elements. The Adjustable reversible eye tension rings can be configured to fit a specific patient's range in canal dimensions in some embodiments.

In some embodiments, the adjustable reversible self-expanding eye stents (SESs) or eye tension rings (ETRs) could include one, two, or more fixation elements. The fixation elements can promote fixation of the SES to the canal wall. In some embodiments, the SES may include a protrusion or indentation for stabilizing and/or fixing the SES at the wall. The fixation elements can also include sub-elements to anchor the SES to the wall, for example, grooves, teeth, ridges, or a saw-tooth pattern, for example. In some embodiments, two or more of the same or different fixation elements can be used in combination.

In some embodiments, the SES can include one or many features such as grooves or loops to allow easy capture and removal of the SES, if/when needed.

Also disclosed herein are various materials for the SES including: shape-memory alloy (SMAs), flexible metals such as stainless steel, titanium, etc. and flexible polymers including shape memory polymers (SMPs), silicone, polyvinylidene fluoride (PVDF), polymethylmethacrylate (PMMA), polypropylene (PP), polyethersulfone (PES), poly-lactic acid (PLA), poly-glycolic acid (PGA), and tunable biodegradable polymers, that can be implanted through a small incision and spring back to the original configuration without damage. In some embodiments, the SES material may include coatings to prevent degradation and encrustation. The coating might be of hydrophobic or hydrophilic in nature such as silicone or polytetrafluoroethylene, or other lubricious coating. In some embodiments, the SES may include a drug-eluting coating on the surface or in the matrix/bulk to further promote healing of the eye.

In some embodiments, disclosed is a method of surgically implanting the SES. A delivery system may contain a cannula for incision into the channel and a trigger mechanism to deploy the SES with each click or turn. The SES can be preloaded for the various sizes into a cartridge which can be attached to the delivery system. The advantage of such a technique is to accurately position the SES to deploy in the appropriate zones within the canal. The SES can be implanted via a placement tool allowing use of the manipulating features which can also be used to easily relocate or retract in some cases. The SES could be implanted alone, or in combination with other SES in some embodiments.

The SES can be customized for a specific patient, including age, race, demographic, predispositions, canal dimensions, anatomical differences, and other factors unique to the patient. The SESs can also be customized based on the patient's baseline IOP or desired IOP reduction by choosing the length and width of the SES and control dilation, and hence the aqueous outflow. Due to the unique features of the SES device and the delivery technique, the device may offer several advantages including maximum dilation of the canal with the material presence within the canal, non-blockage of the lymphatic draining/collector channels for adequate drainage, nano/micro incision surgery with the least amount of material interaction with tissue, and complete reversibility.

In some embodiments, a device can include any combination of the following features, or others as disclosed herein:

An adjustable self-expanding eye stent (SES) or Eye Tension Ring (ETR) embodiment stored and loaded into a delivery system, once deployed the stored embodiment will spring and take shape with its shape memory and form a tension or torsion ring or rings that is inside or outside the canal wall and is larger than the canal diameter, providing separation between the previously compressed canal of the Schlemm's canal or uveolymphatic vessel any animal. One or more embodiments with varying sizes can be deployed in the compressed canal at various locations. The embodiments can be a combination of smaller diameter at the ends and larger diameter in the middle (to anchor and prevent migration) or the same SES can contain these variations.

An SES made of round/rectangular/square polymer or metal or alloy wire/tubing. The wire tubing OD can be between 0.0005" to 0.10". The non-circular wire embodiment can be between 0.0005"-0.10"×0.0005"-0.10"

An SES shaped to match the radius or arc of the perimeter of the globe or uveolymphatic canal path. In some embodiments, the shape may exert no bowing or contracting of the canal. In some other embodiments the shape may have an inward bowing of the canal.

An SES with shallow or variable pitch across the length of the SES. The pitch of a helical SES may vary from 0.00005" to 0.10". In some embodiments, the tighter pitch can be either on the proximal end, or distal end or both. In some embodiments, the wider pitch can be either on the proximal end, or distal end or both.

An SES with a rigidity that permits it to be pushed linearly into Schlemm's canal without losing its integrity/without deforming.

An SES where the distal and proximal ends are open. In some embodiments, the SES may have one or more coils that are welded together to form a closed loop at any point or points along the length, or ends, of the SES. In some other embodiments, the SES pitch of the distal end, proximal end, or both ends, are shallow such that the coil comes back on itself to form a closed loop. In some other embodiments, the SES's proximal end, or distal end, or both are welded to the preceding or subsequent coil to complete a loop.

An SES where one end, or both ends, of the SES are wound tightly such that Schlemm's canal is collapsed by the tightly wound coils thereby allowing flow between Schlemm's canal and the trabecular meshwork through the tightly wound coils and down the length of the tightly wound portion or portions.

An SES comprising of various perforations and extensions to anchor to the canal wall.

An SES comprising a plurality of perforations or features to allow rapid exchange, repositioning, or removal.

An SES designed and selected based on patient specific IOP through pre-operative measurement.

An SES designed with irregularities on the peripheral circumference including ridges, indentations, etc. to allow better anchoring and preventing migration.

An SES implanted in the same operative procedure as positioning another SES in the Schlemm's canal of the patient.

An SES designed to vary the sweep between 10 to 360 degrees. Additionally, the SESs may have multiple continuous or dis-continuous sweeps from 1 to 10.

An SES used in multiples and with various sizing within the canal to control the shape of the expansion and amount and direction flow.

An SES where the SESs can be customized for a specific patient or animal, including age, race, demographic, genetic predispositions, canal dimensions, Schlemm's canal dimensions, intraocular pressure (IOP) measurements, anatomical differences in the eye, and other factors unique to the patient or animal.

An SES where the SES is a tension ring which can be customized to shrink and/or lengthen upon adjusting the manipulating feature of the SES, for safe and easy relocation, repositioning or removal.

An adjustable self-expanding eye stent (SES) or an Eye Tension Ring (ETR) embodiment stored and loaded into a delivery system, once deployed the stored embodiment will spring and take shape with its shape memory and form a tension or torsion ring or rings that is inside or outside the canal wall and is larger than the canal diameter, providing separation between the previously compressed canal of the Schlemm's canal in the body of any animal. A balloon catheter or incision cannula may be deployed prior to the deployment of the SES to allow enlargement of the Schlemm's canal allowing the SES to be deployed with ease.

An SES where the SES has a sharp leading edge or cannula that can pierce the canal wall to anchor and keep it expanded from outside the canal wall.

An SES where the SES has a manipulating feature that is anchored inside the canal wall to allow subsequent manipulating of the SES.

An SES where the SES can be delivered in a shrunken (or smaller) state by manipulating temperature of the SES using external energy (electrical, mechanical, thermal, RF, light, etc.)

An adjustable self-expanding eye stent (SES) or an Eye Tension Ring (ETR) embodiment that can be manipulated by an insertion tool whose temperature can be externally controlled through an energy source (electrical, mechanical, thermal, RF, light, etc.), such that it can alter the shape (shrink or expand) of the SES to make insertion or retrieval procedure both minimally invasive, responsive, and easy to manipulate/handle.

An SES comprising an extruded metal or plastic tubing may be stored in a first state, and once the SES is deployed to the desired location, the SES takes shape with its shaped memory and configuration.

An SES comprising an extruded metal or plastic tubing whereby the extruded metal or plastic tubing is printed with measurement markers to serve as a reference point in SES deployment.

An SES with a cannula and/or balloon at the distal end which can facilitate opening of the Schlemm's canal and anchoring from the canal incision/opening to accurately deploy and position the SES.

An SES which a user can feel being incrementally advanced towards the distal shaft as guided by the delivery device. The deployment mechanism can be conveyed from the handle of the device. The deployment mechanism can be geared so that the advancement is measured based on the predetermined measured location.

A stapler-type device where the SES is stored in a cartridge containing a predetermined count such as 1 to 6 SES's with single SES's individually dispensed from the cartridge via a trigger mechanism from the handle of the SES delivery system.

An SES delivery system having the SESs pre-loaded into multiple cartridges allowing deployment of all SESs in one single procedure minimizing time needed.

An SES delivery system which can be either manually via pusher catheter—shaft/tubing; or mechanically driven e.g., staple; or electromechanically delivered into the desired location; and or energy driven i.e. radio frequency, or electronic signal.

An SES that may have features such as a loop, hook, or eyelets to allow easy capture using an SES retrieval system that can allow the SES to compress and withdraw into the system in cases where repositioning or removal is desired.

An SES can be withdrawn by compression or re-folding the embodiment back into a linear or FIG. 8 shape and either fully withdrawn or reposition.

The SES can be withdrawn by capturing the manipulating feature of the SES and re-winding into a track/guide.

An SES that can be withdrawn by capturing the manipulating feature and shrinking the SES by manipulating temperature of the SES using external energy.

SES delivery systems and SES retrieval systems that have polymeric coatings including fluoropolymers and silicone, etc. The coatings may also be used to seal and prevent coagulation, debris accumulation, or degradation over time.

An SES can be deployed using a tool and/or mechanism to hold both sections of the SES align with the axis of the SES. After which the SES is repositioned by turning the SES perpendicular to the deployed axis.

An SES with customized sizing based on biometry of the Schlemm's canal space. The Schlemm's canal may be measured or imaged as a pre-operative scan using various qualitative or quantitative measurement tools to determine the customized fit of SES size(s) required for the specific patient's need. Biometric measurements including Schlemm's canal dimensions, Schlemm's canal angle, cross-sectional area (CSA), may be used to determine and customize the SES design to fit the specific physiological and anatomical need of the patient.

An SES with customized sizing based on intraocular pressure reading or biometry of the eye. The IOP can be used to determine the customized fit of SES size(s) required for the specific patient's need or required reduction of IOP.

As the patient ages and as canal and Schlemm's canal undergoes physiological changes, the SES may be replaced (with other sizes or tensile strength) to fit the changing need.

A device for maintaining patency of a uveolymphatic region in the eye or the Schlemm's canal, comprising: a self-expanding shape memory member comprising a proximal end, a distal end, and a passageway therebetween configured to facilitate flow of body fluids therebetween, the shape memory member further comprising a plurality of partial or complete loops between the proximal end and the distal end, the shape memory member comprising a central portion and lateral portions, wherein the central portion comprises a first diameter and the lateral portions comprise a second diameter, wherein the first diameter is not equal to the second diameter, wherein the shape memory member further comprises a first radially compressed configuration transformable to a second radially enlarged configuration.

Such a device wherein the first diameter is larger than the second diameter.

Such a device, wherein the first diameter is smaller than the second diameter.

Such a device wherein the central portion has a generally constant first diameter throughout the entire length of the central portion.

Such a device wherein the lateral portions have a generally constant second diameter throughout the entire length of the central portion.

Such a device, wherein non-adjacent loops of the device are only connected to each other via directly adjacent loops.

Such a device, wherein the shape memory member has a diameter of between about 0.0005" and about 0.050".

Such a device wherein the shape memory member has a non-circular cross section, the cross-section having a major axis and a minor axis, wherein the minor axis dimension is between about 0.0005" and about 0.050".

Such a device wherein the radius of curvature of the device matches that of the radius of curvature of the uveolymphatic canal in the globe.

Such a device wherein the radius of curvature of the device may have an inward or outward bowing of the canal.

Such a device wherein the proximal end of the device may have a pitch dimension between 0.0005" and about 0.050".

Such a device wherein the distal end of the device may have a pitch dimension between and about 0.050".

Such a device wherein the main body of the device may have a pitch dimension between 0.0005" and about 0.050".

Such a device wherein the proximal and/or distal end of the device may have a smaller pitch in comparison to the main body.

Such a device wherein the proximal and/or distal end of the device may have the coil ending in the same plane as a closed loop finish.

Such a device wherein the proximal and/or distal end of the device may be polished via mechanical, chemical, or electrochemical methods.

Such a device wherein the proximal and/or distal end of the device may be welded to the preceding or subsequent coil to complete a loop.

Such a device wherein one end, or both ends, of the device are wound tightly such that Schlemm's canal is collapsed by the tightly wound coils thereby allowing flow between Schlemm's canal and the trabecular meshwork through the tightly wound coils and down the length of the tightly wound portion or portions.

Such a device further comprising one or more manipulation features proximate at least one of the proximal ends and the distal end.

Such a device wherein the one or more manipulation features are selected from the group consisting of an eyelet, a hook, and a loop.

Such a device wherein the one or more manipulation features are selected from the group consisting of an eyelet, a hook, and a loop.

Such a device, wherein the manipulation features are used for anchoring into the canal.

Such a device wherein the shape memory member comprises a biodegradable polymer with controlled resorption into the eye.

Such a device wherein the shape memory member comprises a drug-eluting member coated on the surface or embedded into the bulk for controlled release into the eye.

Such a device wherein the shape memory member comprises a hydrophobic coating.

Such a device wherein the shape memory member comprises a hydrophilic coating.

Such a device wherein the proximal end comprises a sharp edge configured to pierce the canal wall to anchor into the canal wall itself and keep it expanded from outside the canal wall.

Such a device, wherein the shape memory member comprises surface irregularities configured to promote anchoring and/or prevent migration.

Such a device wherein the surface irregularities comprise one or more of ridges, roughened surface, pores, and indentations.

Such a device comprising between about 1 and about 100 partial or complete loops.

Such a device wherein the device has by-pass and/or dilating feature(s) at the entry or exit or along the length of the device, into or out of the canal to/from the anterior chamber.

Such a device wherein the device has by-pass features into the anterior chamber for aqueous flow at the entry, or exit or along the length of the device, into or out of the canal to/from the anterior chamber.

Such a device, wherein the device has elongated diameter in certain sections where by-pass and/or dilating feature(s) are desired, at the entry or exit or along the length of the device, into or out of the canal to/from the anterior chamber.

Such a device wherein the device may be implanted using fluorescence or image-guided to avoid blocking of collector channels within the canal.

Such a device wherein the device may be a wire shaped to various configurations to self-expand in the canal and maintain patency.

Such a device wherein the device may be of specific dimensions in outer diameter, pitch, wire diameter, and shape to accommodate the required tension needed within the canal.

Such a device, assisted by finite element modeling for selective patient population groups.

Such a device, wherein the device has a polymeric sheath along the length of device in a continuous or non-continuous manner.

A delivery system comprising a such a device and a delivery tool comprising a device channel comprising an outer sheath and an inner member, the device configured to be disposed between the inner member and the outer sheath, the delivery tool comprising a locking member configured to reversibly lock the device within the device channel.

Such a delivery system wherein the delivery may be accessed from the angle inside the anterior chamber, or outside the eye from the sub-conjunctival region or the limbus region or the scleral region.

Such a delivery system assisted with dying or visualization to access the canal in a minimally invasive manner.

Such a delivery system, wherein the delivery tool comprises a scope or visualization.

Such a delivery system wherein the delivery tool has a pressured system to control the delivery of the device.

Such a delivery system wherein the delivery tool is attached to a syringe.

Such a delivery system wherein the delivery tool has a temperature control to manipulate the state of the device before, during and after delivery.

Such a delivery system wherein the inner, outer members and the device may be controlled using sliders or plungers.

Such a delivery system wherein the inner, outer members and the device may be controlled using torsional or axial contact boards.

Such a delivery system wherein the inner, outer members and the device may be controlled using torsional or axial contact rollers.

Such a delivery system wherein members may provide the incision required to enter the uveolymphatic vessel or canal.

Such a delivery system wherein it may have an un-coiler channel to reduce friction in delivery the device.

Such a delivery system wherein it may pre-tighten or wound-up the device.

Such a delivery system where it may be powered by a piezo-electric or vibrational motor.

Such a delivery system, where it may use a guide-wire to deliver the device.

Such a delivery system where it may use a guide-wire to reposition or retract the device.

A method of treating glaucoma in a patient, comprising expanding the uveolymphatic channel or the Schlemm's canal in the patient using an expandable member, radially expanding at least one device comprising a shape memory member comprising a plurality of windings within the canal of the Schlemm's canal to expand the diameter of the Schlemm's canal, at least one device comprising a larger diameter portion and a smaller diameter portion, the larger diameter portion providing a radial force against the Schlemm's canal sufficient to maintain patency of the Schlemm's canal, and unlocking a manipulation feature of the at least one device from a delivery tool.

Such a method wherein the expandable member comprises a balloon.

Such a method comprising radially expanding a plurality of devices.

Such a method wherein the plurality of devices is radially expanded sequentially.

Such a method wherein the plurality of devices comprises varying sizes and/or shapes.

Such a method, further comprising removing the delivery tool from the Schlemm's canal.

Such a method wherein the delivery tool comprises a scope comprising a device channel, an outer sheath, and an inner member, wherein the device is disposed between the inner member and the outer sheath and in a radially compressed configuration during delivery.

Such a method further comprising axially moving the outer sheath relative to the device to allow the device to radially expand.

Such a method wherein following radially expanding the at least one device within the canal of the Schlemm's canal, no more than about 25% of an entire surface area of the device is exposed to aqueous flow within the Schlemm's canal.

Such a method wherein the shape memory member has a maximum diameter of less than about 0.050".

Such a method wherein the device once implanted does not extend axially outside of the Schlemm's canal.

Such a method further comprising delivering energy to the at least one device to transform the size and/or shape of the device.

Such a method, wherein the at least one device is custom created based on biometry of the patient's Schlemm's canal.

Such a method wherein the at least one device is custom created based on measured patient parameters selected from one or more of pre-operative imaging, Schlemm's canal dimensions, Schlemm's canal cross-sectional area, Schlemm's canal perimeter.

Such a method wherein the at least one device is custom created based on measured patient preoperative intraocular pressure IOP and desired regulation of IOP.

A method of treating glaucoma in a patient, comprising dilating or by-passing the uveolymphatic channel or the Schlemm's canal in the patient using an expandable member, radially expanding at least one device comprising a shape memory member comprising a plurality of windings within or across the Schlemm's canal to provide by-pass and/or expansion into the diameter of the Schlemm's canal, at least one device comprising a larger continuous diameter portion and a smaller diameter portion, the larger diameter portion providing a radial force against the Schlemm's canal sufficient to maintain patency of the Schlemm's canal.

Such a method wherein the device has by-pass and/or dilating feature(s) at the entry or exit or along the length of the device, into or out of the Schlemm's canal to/from the anterior chamber.

Such a method wherein the device has by-pass feature(s) at the entry and/or exit or along the length of the device, into or out of the Schlemm's canal to/from the anterior chamber at the wound and/or incision.

Such a method wherein the device has by-pass feature(s) at the entry and/or exit or along the length of the device, along the same perimetric plane of the Schlemm's canal away from the anterior chamber at the wound and/or incision.

Such a method where one end, or both ends, of the device are wound tightly such that Schlemm's canal is collapsed by the tightly wound coils thereby allowing flow between Schlemm's canal and the trabecular meshwork through the tightly wound coils and/or down the length of the tightly wound portion or portions.

Such a method where one end, or both ends, of the device are wound portion or portions protrude through the wall of canal into the trabecular meshwork such that flow between canal and trabecular meshwork is enabled through the tightly wound coils and/or down the length of the tightly wound portion or portions.

Such a method, wherein the device has a polymeric sheath along the length of device in a continuous or non-continuous manner.

A method of repositioning or removing a device for treating glaucoma in a patient, comprising delivering an effector tool proximate the Schlemm's canal and a previously implanted device residing within the canal of the Schlemm's canal, wherein a previously implanted device comprises one or more shape memory member comprising a plurality of windings, the windings forming a canal with a variable inner diameter, the device maintaining the patency of the canal of the Schlemm's canal, contacting a manipulation feature of the previously-implanted device with the effector tool, locking the manipulation feature of the at least one device; and removing or repositioning the device.

Such a method further comprising delivering energy from the effector tool to the manipulation feature to change the size and/or shape of the device.

Such a method wherein the manipulation feature comprises a hook, a loop, a magnet, or a threaded feature.

Such a method wherein the manipulation feature comprises a hook, a loop, a magnet, or a threaded feature.

BRIEF DESCRIPTION OF THE DRAWINGS

FIG. 3A shows a cross-sectional stained micrograph of the human eye with the Schlemm's canal's location clearly labeled.

FIGS. 3B-3D show detailed developmental cellular schematics of the uveolymphatic vessel, including how aqueous humor outflow occurs.

FIGS. 5A and 5B contain variants of the self-expanding eye stent (SES) device in a helical form with the manipulating features and tension rings. FIG. 5A contains a variant of the SES device where the central portion of the tension ring is larger in diameter than the peripheral ends.

FIG. 5C contains a variant of the SES device where the central portion of the tension ring is smaller in diameter than the peripheral ends.

FIGS. 11A-11J illustrates variants of the SES device where the device has variable shapes and sizes along the free length of the helical coil of the SES.

FIG. 12 illustrates a variant of the SES device where the manipulation feature allows a hook-loop to reposition or retrieve the SES.

FIGS. 13A and 13B illustrate a variant of the SES device where the helical coil has a polymeric sheath at the entry or exit or through the length of SES allowing regulation of flow into the canal.

FIGS. 18A-18C illustrates a variant of an SES delivery device containing an outer cannula that houses an inner cannula that in turn houses the SES device. Sliders to move the cannulas and the device are highlighted.

FIGS. 26C and 26C-1 illustrate a variant of a curved and electropolished SES device in situ in the uveolymphatic canal with the proximal end extended along the same plane as the channel to create a collapsed wound opening and by-pass for fluid flow.

DETAILED DESCRIPTION OF THE INVENTION

Several factors influence the onset and progression of glaucoma as discussed in previous sections. The critical region where aqueous drainage occurs is in the uveolymphatic vessel or Schlemm's canal. When this region is blocked or constricted, it creates a cascading effect of inflammation that includes edema or elevation of intraocular pressure. Dilating and/or creating by-pass flow for the uveolymphatic vessel or Schlemm's canal allows for continuous and regulated clearance of the aqueous humor, which restores the lymphatic function of the eye and hence regulates the intraocular pressure.

Disclosed herein are adjustable self-expanding eye stent (SES) or reversible eye tension rings (ETRs) embodiments that can be configured to adjust the diameter and opening of the Schlemm's canal. SESs can include various generally prosthetic devices, including tubular members configured to maintain or improve the patency of at least a portion of the uveolymphatic vessel, such as the Schlemm's canal 400. In some embodiments, a device can improve the patency of the Schlemm's canal, but not other uveal regions.

Figure 4A:
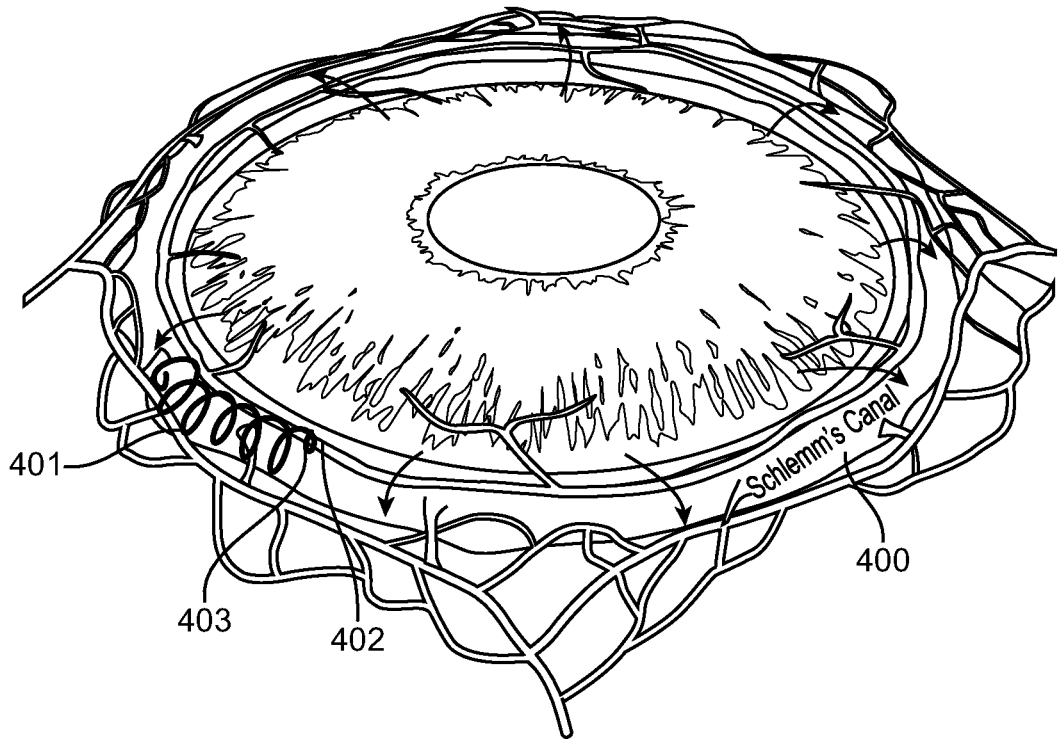
FIG. 4A illustrates an isometric sketch of the eye with a variant of the self-expanding eye stent (SES) device in a helical form dilating the uveolymphatic vessel or Schlemm's canal FIGS. 4B and C illustrate variant of the SES device in a helical form with the manipulating features and tension rings in axially expanded and contracted configurations.

Disclosed herein are methods for deploying prosthetic devices, including fixed canal or adjustable self-expanding eye stent (SES) or reversible eye tension rings (ETRs) 401 using an expandable member, such as a balloon technique, expandable device (e.g., movable cage with struts). In some embodiments, the leading edge of the delivery device for the SES or a cannula can create an entry incision 402 such that the SES 401 can be delivered in a folded state. Once inside the canal 400, the SES 401 can be fully deployed and uncoil in-situ, as shown in FIG. 4A. The SES 401 may contain one or more manipulation features 403 such that they can be used to adjust, reposition, and retrieve to/from and within the uveolymphatic vessel. In some embodiments, the deployment of the SES 401 can be controlled by a spring-loaded plunger or threaded screw type tool. Some embodiments of the SES 401 can be deployed into the balloon expanded canal, such that it anchors or keeps the canal expanded and away from collapse. In some embodiments, multiple SESs 401 can be deployed in various locations within the canal 400 and allow regulation of the flow through controlled dilation along the length of the canal and/or by-pass of fluid within the canal.

Disclosed herein are manipulation features 403 contained within the devices, such as SES 401. In some embodiments, the SES 401 can include one, two, or many manipulating features 403 such as barbs, grooves or loops to allow easy anchoring, capture, re-alignment, repositioning and removal of the SES 401, if/when needed. The manipulation feature may be on or off axis, inside or outside the canal wall, and penetrating or non-penetrating with respect to the canal wall. One key aspect of the manipulation feature in the SES in some embodiments is to allow control for reversibility of the procedure.

Figure 4B:
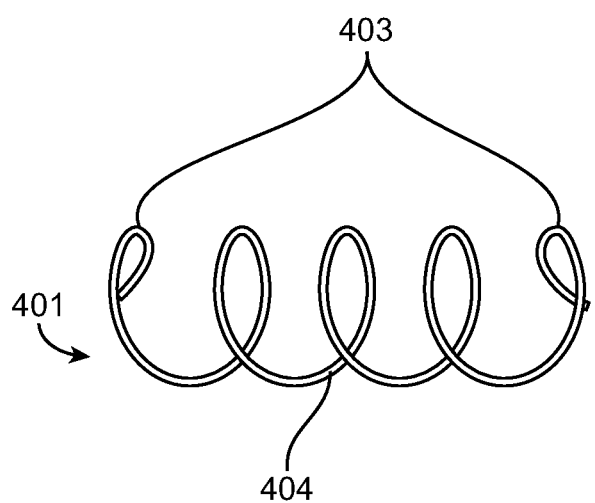
Figure 4C:
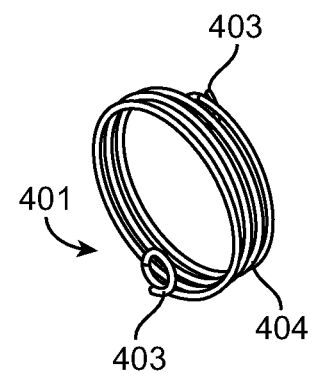

Disclosed herein are various methods of removing the prosthetic devices, including SES 401, in cases where reversibility or repositioning is desired. In some embodiments, a minimally invasive retrieval device can be deployed via the containing a retrieval wire with a feature that links with the manipulating feature 403 in the SES 401, as shown in FIG. 4B. In some embodiments, the manipulating feature 403 can be linked via a hook-loop, hook-hook, or loop-hook type set-up. In some embodiments, one or both of the retrieval or manipulating feature 403 can include complementary magnets, a gripper including, for example, movable jaws, an adhesive, a suction mechanism, and the like. In some embodiments, the retrieval device may wind-in the SES 401 into a track or threaded feature within the devices. The insertion, anchoring/connection to 403 and the removal of the SES 401 may all be performed by external controls (outside the body) of the devices in some cases.

Disclosed herein are embodiments of prosthetic devices such as SES 401 in a wire form with a manipulating feature or features 403 at the proximal or distal end of the SES. FIG. 4B illustrates various views of such an embodiment. The manipulating feature can be, for example, an eyelet 403 extending radially inwardly or outwardly in other embodiments, or other features as disclosed elsewhere herein.

Disclosed herein are embodiments of prosthetic devices such as SES 401 in a flat or angulated ribbon form with a manipulating feature or features 403 at the proximal or distal end of the SES. For example, the structure could be generically helical with a plurality of revolutions as shown, with a flattened cross-section such as oval or rectangular for example. FIGS. 5A-5C illustrate various views of an embodiment of the SES 401 where the tension rings 404 are continuous along the length of the SES 401, but in varying diameter. In other embodiments, either or both of the central or lateral portions can have gradual or stepped variable diameters. Manipulation features 403, such as eyelets or other disclosed herein, can be attached, connected, or integrally formed at one or both ends of the device, or at other locations, and be made of the same, or different materials as the rest of the device itself. In some embodiments, the expanded length and/or number of rotations of the larger diameter central portion is about, or no more than about 50%, 60%, 70%, 80%, 90%, or more of that of the entire expanded length and/or number of rotations of the device.

Disclosed herein are methods for deploying prosthetic devices, such as adjustable reversible self-expanding eye stents (SESs) or eye tension rings (ETRs) within the Schlemm's canal. In some embodiments, the leading edge or other portion of the SES 401 can be inserted using an insertion device between the Schlemm's canal. In some embodiments, upon partial or complete insertion, the SES 401 can spring into place, assuming a radially expanded configuration, and keep the Schlemm's canal wide-open, due to the shape-memory nature of the SES 401 material. In some embodiments, multiple SESs 401 of similar or varying diameters can be deployed within the depending on the Schlemm's canal anatomy. Some embodiments can include 2, 3, 4, 5, 6, 7, 8, 9, 10, or more devices, or ranges including any two of the foregoing values, such as between 1 and 10 devices, or between 2 and 8 devices for example. Each device can be placed directly adjacent to, e.g., in contact with each other, overlapping with each other, or spaced apart and not directly contacting each other, or combinations thereof. Additionally, some embodiments may have one, two, or more relatively larger diameter tension rings 404 within the SES 401 relative to other rings of the SES that are either centrally located or positioned elsewhere depending on the anchoring requirements within the Schlemm's canal. In other embodiments, multiple such SESs 401 may be deployed within the canal. In some embodiments, one large SES could be deployed covering the entire length or perimeter of the Schlemm's canal, with similar or varying diameter along its length, as shown in FIG. 5A or 5B.

Figure 6A:
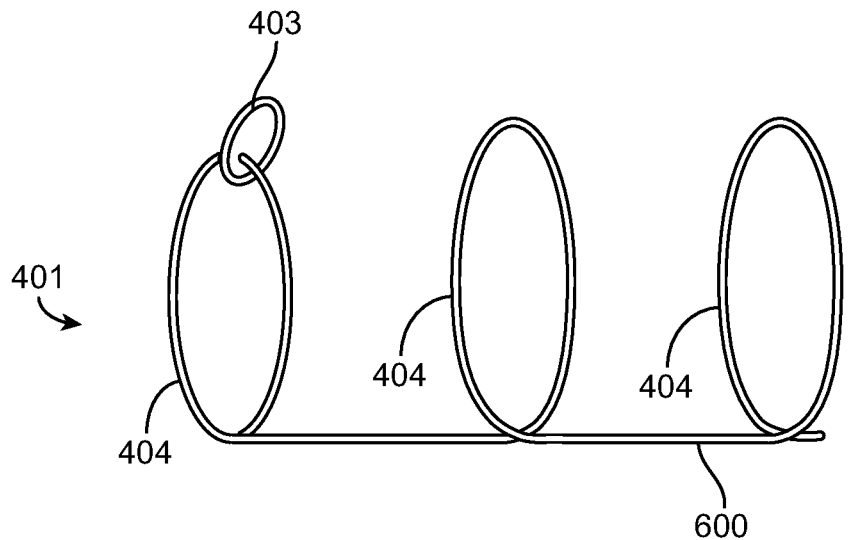
FIG. 6A illustrates a variant of the self-expanding eye stent (SES) device where the device is connected by a structural feature holding the multiple tension rings.
Figure 6B:
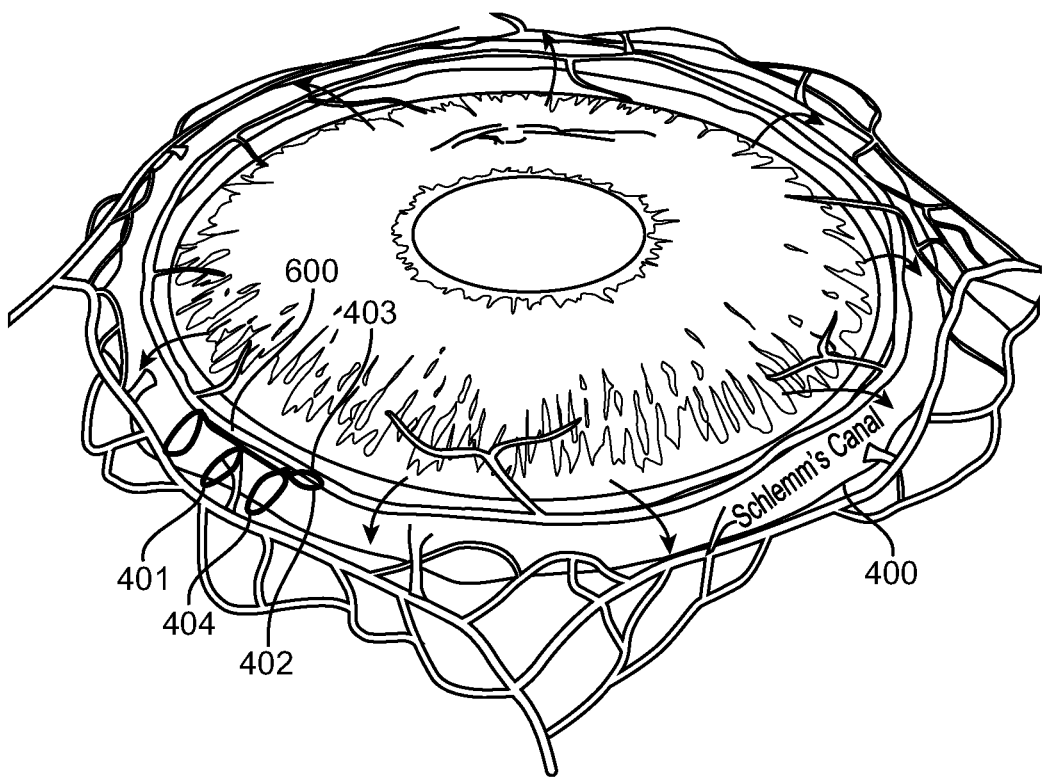
FIG. 6B illustrates a variant of this SES device dilating the uveolymphatic vessel or Schlemm's canal.

Disclosed herein are embodiments of prosthetic devices, including SES 401 that can connect eye tension rings 404 via a connecting anchor or support structure 600 for stability, as shown in FIGS. 6A and 6B. In some embodiments, there may be several of the eye tension rings 404 connected in a similar continuous or separate manner.

Figure 7A:
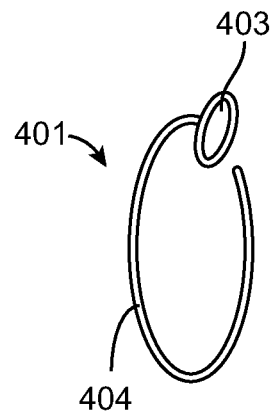
FIG. 7A illustrates a variant of the self-expanding eye stent (SES) device where the device is a single tension ring with a manipulating feature.
Figure 7B:
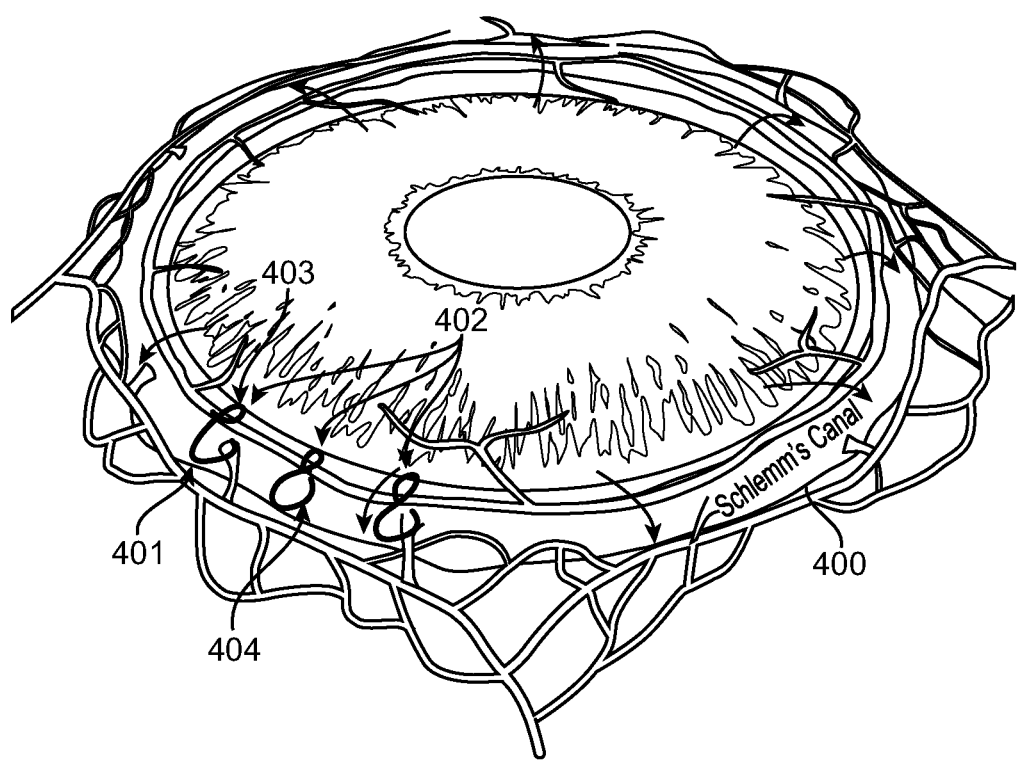
FIG. 7B illustrates a variant of this SES device dilating the uveolymphatic vessel or Schlemm's canal in multiple locations within the canal.

Disclosed herein are embodiments of prosthetic devices, including SES 401 that are non-continuous independent tension rings 404 with a manipulating feature 403 (that may be positioned outside or inside the canal 400), as shown in FIGS. 7A and 7B. In some embodiments, these SESs 401 may be inserted one at a time or several across various locations within the canal 400.

Figure 8A:
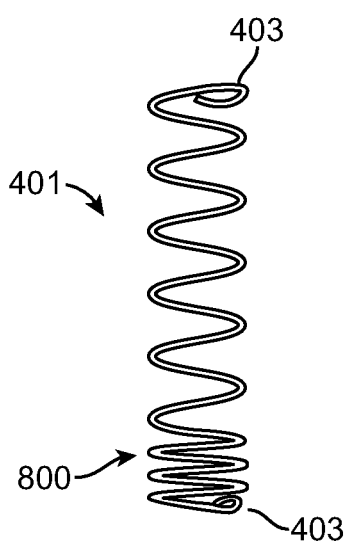
FIGS. 8A and 8B illustrate variants of the self-expanding eye stent (SES) device where the device has variable pitch with an entry by-pass feature and a manipulating feature.
Figure 8B:
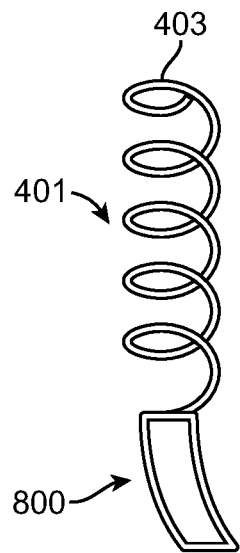
Figure 8C:
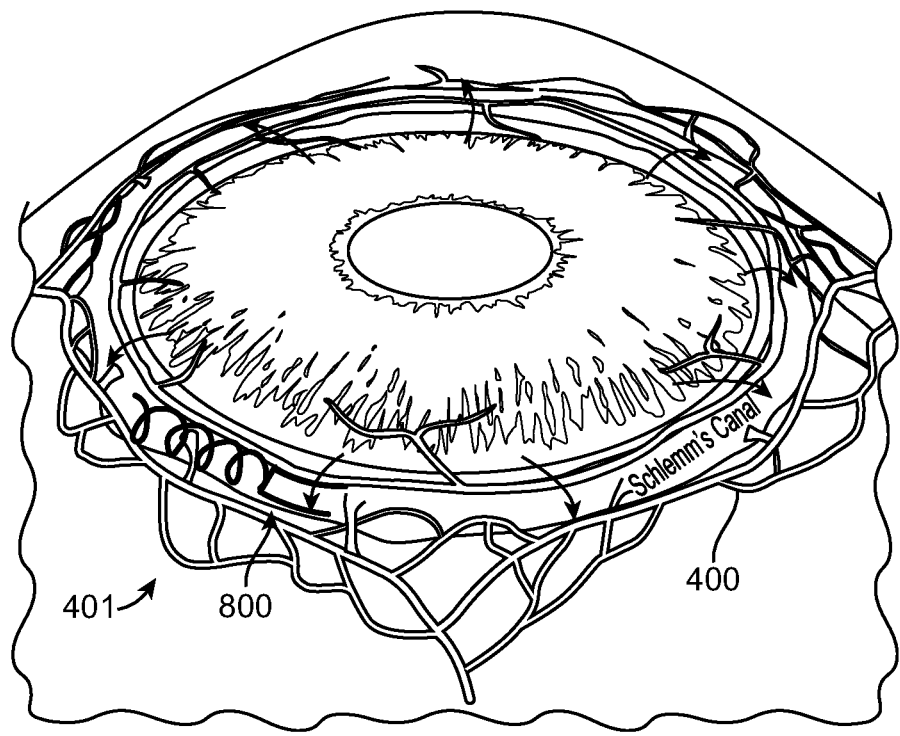
FIG. 8C illustrates a variant of this SES device dilating the uveolymphatic vessel or Schlemm's canal while the by-pass feature is within or through the canal wall.

Disclosed herein are embodiments of prosthetic devices, including SES 401 that are of variable pitch and length, as shown in FIGS. 8A and 8B. The SES 401 may have a by-pass and/or dilating feature 800 to regulate aqueous flow through the canal and/or by-pass of fluid within and across the canal. This feature 800 may be at the entry of the canal wall as shown in FIG. 8C, which may also serve to anchor the SES 401 in the canal along with ease of manipulation to reposition or retrieve the SES 401 device within or away from the canal.

Figures 9A, 9B, 9C, 9D:
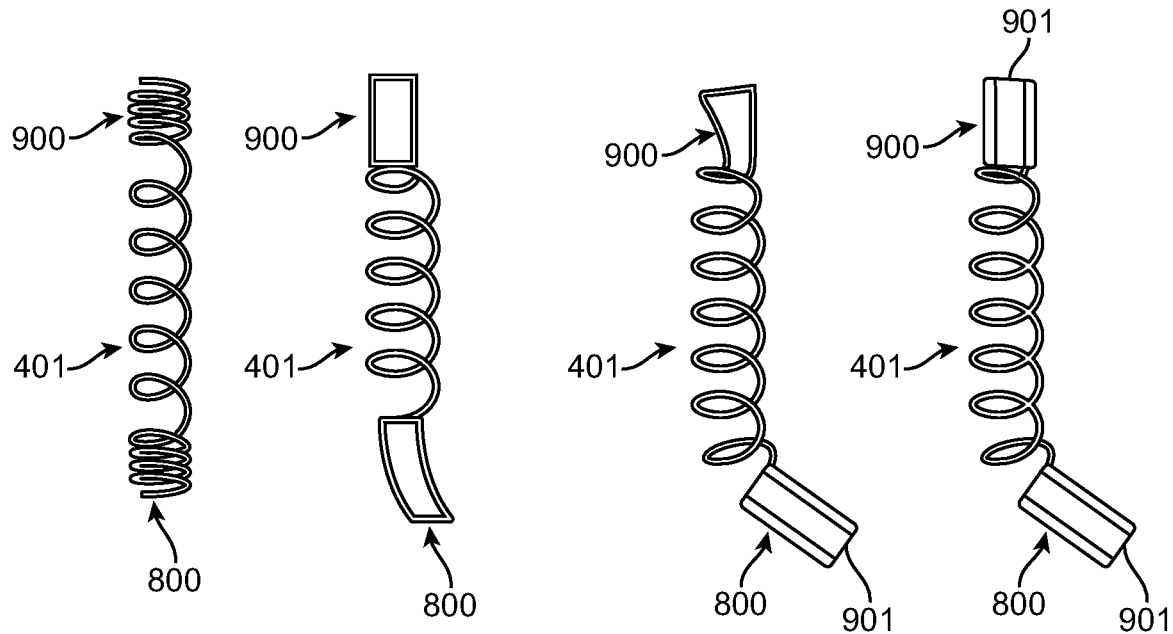
FIGS. 9A-9D illustrate variants of the SES device where the device has variable pitch with a double entry by-pass features and manipulating features.
Figure 9E:
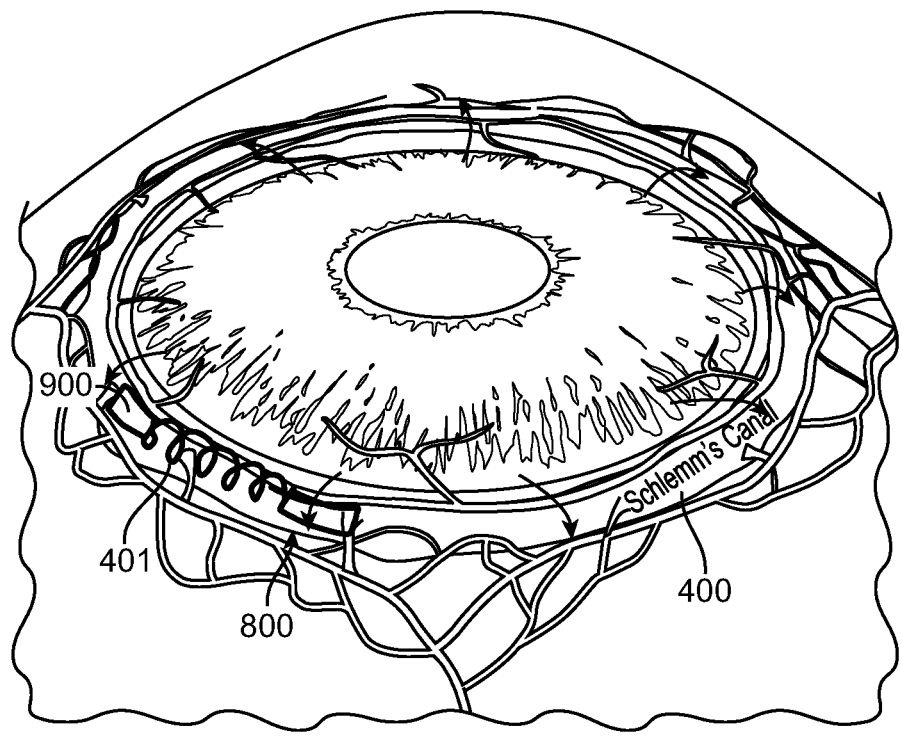
FIG. 9E illustrates a variant of this SES device dilating the uveolymphatic vessel or Schlemm's canal while by-pass features at either end are within or through the canal walls.
Figure 10A:
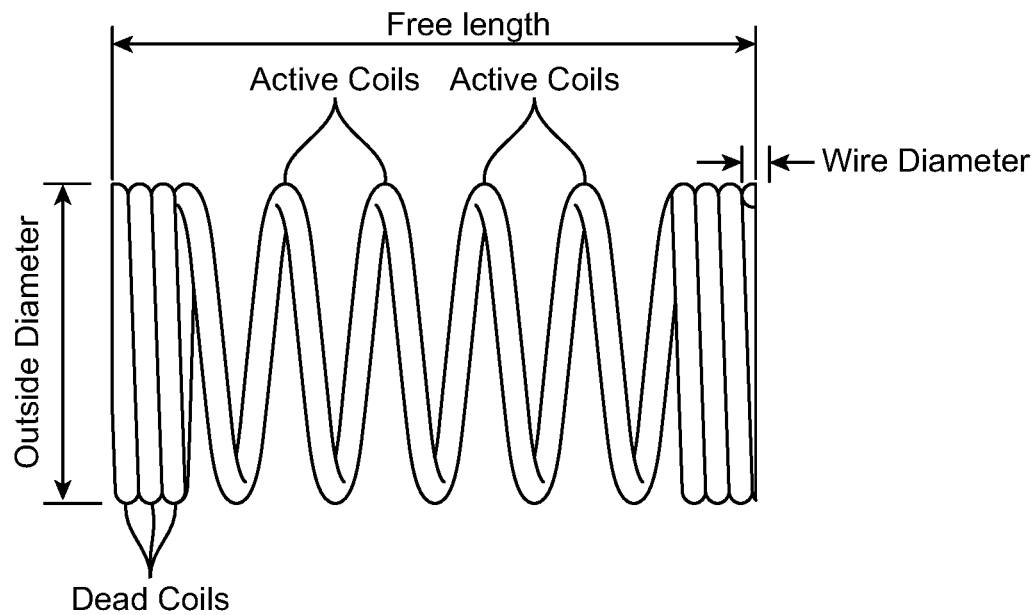
FIGS. 10A-10F illustrates variants of the SES device where the device has variable pitch along the free length of the helical coil of the SES.
Figure 10B:
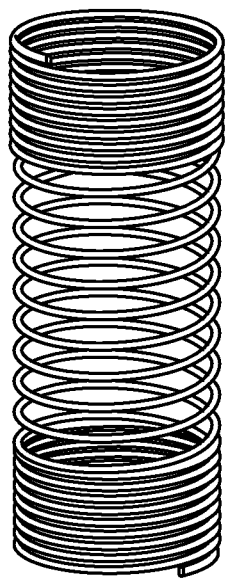
Figure 10C:
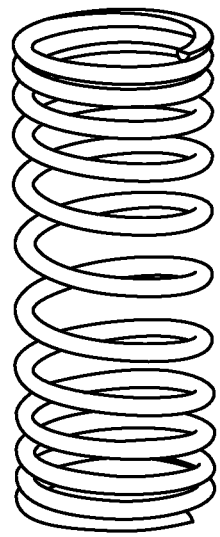
Figure 10D:
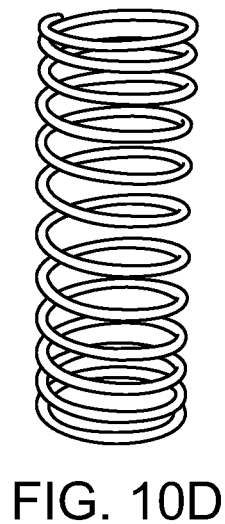
Figure 10E:
Figure 10F:
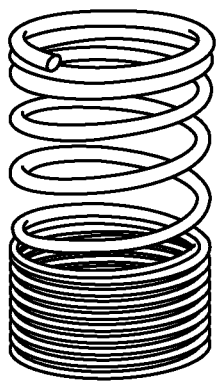

Disclosed herein are embodiments of prosthetic devices, including SES 401 that are of variable pitch and length, as shown in FIGS. 9A-9D. The SES 401 may have multiple by-pass and/or dilating features 800 and 900 to regulate aqueous flow through the canal and/or by-pass of fluid within and across the canal. These features 800 or 900 may be at each end of the SES device 401 or continuously along the length of the device 401. These features as shown in FIGS. 9A-9D may also serve to anchor the SES 401 in the canal along with ease of manipulation to reposition or retrieve the SES 401 device within or away from the canal, as shown in FIG. 9E. Additionally, these features may have varying inner diameter 901, similar to tube or channels to control entry and out-flow of fluid across and within the canal. Additionally, the entry access or by-pass features 800 or 900 may be at several locations (2, 3, 4, 5, etc.) along the length of canal and may be fully enclosed within the canal, or partially or fully across the canal into the anterior chamber.

Disclosed herein are embodiments of prosthetic devices, including SES 401 that are of variable pitch across the free length of the SES 401, as shown in FIGS. 10A-10F. The variation of the pitch of the helical coil of the SES 401 may be utilized to regulate and customize dilation, by-pass, anchor, and manipulation of the SES 401 to regulate aqueous flow and IOP.

Disclosed herein are embodiments of prosthetic devices, including SES 401 that are of variable pitch and diameter and shape across the free length of the SES 401, as shown in FIGS. 11A-11J. The variation of the pitch and diameter of the helical coil along the free length of the SES 401 may be utilized to regulate and customize dilation, by-pass, anchor, and manipulation of the SES 401 to regulate aqueous flow and IOP.

Disclosed herein are embodiments of prosthetic devices, including SES 401 that have unique shapes, such as hooks or C-loops or rings or eyelets to control positioning, deployment, anchoring, removal, retrieval, and general manipulation of the SES 401. These features may allow the SES 401 to regulate and customize dilation, by-pass, anchor, and manipulation of the SES 401 to regulate aqueous flow and IOP.

Disclosed herein are embodiments of prosthetic devices, including SES 401 that have a polymeric sheath across the SES 401. Certain embodiments as shown in FIGS. 13A and 13B may have the sheath across the coil of the SES 401 at the entry, exit, center, or various zones within the length of the SES 401, or continuously through the entire length of SES. This sheath may allow regulation and customization of dilation, by-pass, anchor, and manipulation of the SES 401 to regulate aqueous flow and IOP. The polymeric sheath may be made of various degradable and non-degradable polymers, including polytetrafluoroethylene (PTFE), silicone, lubricants, degradable polymers, hydrophobic polymers, hydrophilic polymers, hybrid polymers, etc. The polymeric sheath may be continuous or discontinuous across the length and diameter of the SES 401. The polymeric sheath may be cast, molded, spray-coated, dip-coated, or coated using other techniques over the base metal, alloy or polymeric coil that constitutes the SES 401.

Figure 14:
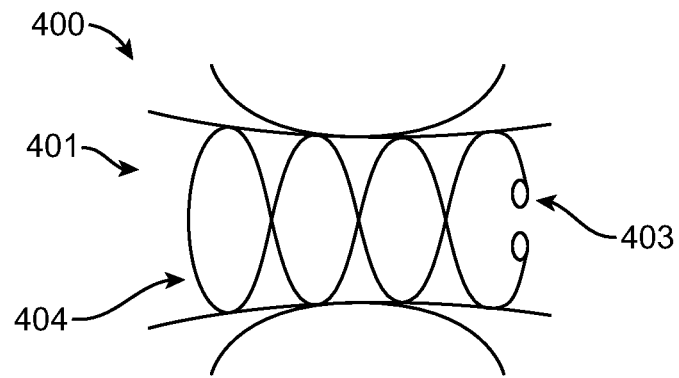
FIG. 14 illustrates a variant of the SES device where the device is a double helical coil with manipulation features.

Disclosed herein are embodiments of prosthetic devices, including SES 401 that can form a double-helix or return pattern as shown in FIG. 14, in some cases with two discrete ends distally and a continuous loop end proximally without free ends. In some embodiments, there are two manipulating features 403 shown with both in the entry plane on the distal end of the device 401, although some embodiments could include only one, or three, four or more manipulating features for example.

Figure 15:
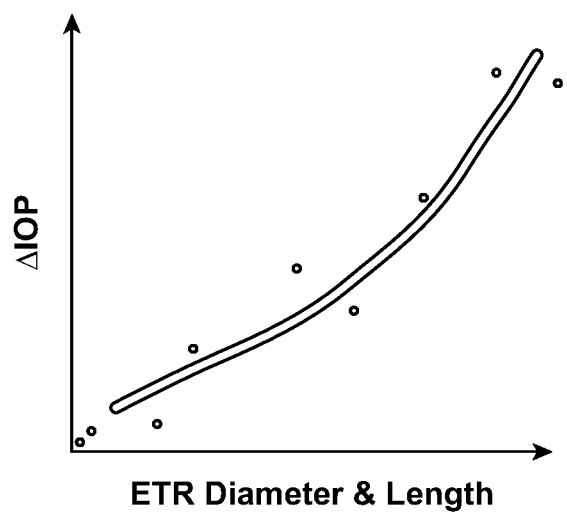
FIG. 15 illustrates a graph demonstrating the correlation of the aqueous flow (and hence change in intraocular pressure or IOP) as a function of the SES diameter and length.

Disclosed herein are embodiments of methods to use pre-operative measurements of the intraocular pressure (IOP) to customize the device, e.g., SES diameter, length, and pitch for the specific requirement of IOP reduction. Yan et al (2016—Schlemm's Canal and Trabecular Meshwork in Eyes with Primary Open Angle Glaucoma: A Comparative Study Using High-Frequency Ultrasound Biomicroscopy, PLOS One, 11 (1) https://doi.org/10.1371/journal.pone.0145824) have demonstrated the correlation of Schlemm's canal diameter to IOP. FIG. 15 shows an example to determine and customize the SES 401 design to fit the desired outflow and thus desired IOP decrease for the specific patient. The aqueous outflow in the uveolymphatic canal can be directly correlated to the extent of dilation of this vessel. One or a plurality of customized devices can then be manufactured and then implanted, e.g., in a separate procedure. However, the sizing procedure and implantation procedure can be combined into a single procedure in other embodiments.

Disclosed herein are embodiments of prosthetic devices, including SES 401 that are configured to be delivered in a minimally invasive form and retain the intended shape in-situ. In some embodiments, the SES may be circular in shape with multiple sweeps (rotations). In some variants, SES 401 may have 2 to 30 total sweeps (or rotations), whole or partial sweeps, such as 2, 3, 4, 5, 6, 7, 8, 9, 10, 12, 15, 20, 25, or 30 sweeps, or ranges including any two of the foregoing values. In some embodiments the pitch (separate between each ring) can be between about 0.0001" and about 0.1", such as about 0.0001", 0.0005", 0.001", 0.002", 0.003", 0.005", 0.05", 0.1", or ranges including any two of the foregoing values Disclosed herein are embodiments that either partially or wholly cover the Schlemm's canal, such as for example, at least about, about, or no more than about 10%, 20%, 30%, 40%, 50%, 60%, 70%, 80%, 90%, 100% of the axial length of the Schlemm's canal, or ranges including any two of the foregoing values The illustrations shown here also demonstrate the manipulation features 901 that allow ease of manipulation, relocation, and retraction using a separate retrieving device. In some embodiments, the implanted SES will not extend axially into any other uveal regions. In some embodiments, the implanted SES extends axially into one or more of the uveal or trabecular meshwork regions.

Disclosed herein are embodiments of prosthetic devices, including SES 401 that are delivered in a minimally invasive form and retain the intended shape in-situ. In some embodiments, the SES may be circular in shape with multiple sweeps (rotations). In some variants, SES 401 may have 2 to 30 total sweeps (or rotations), whole or partial sweeps. In some embodiments the pitch (separate between each ring) can be between 0.0001" to 0.1". Disclosed herein are embodiments that either partially or wholly cover the Schlemm's canal. The illustrations shown here also demonstrate the manipulation features 403 that allow ease of manipulation, relocation, and retraction using a separate retrieving device. In some embodiments, the central portion of the SES may have the largest diameter to allow better anchoring within the Schlemm's canal and prevent migration within the, with gradually decreasing diameters from the central portion to one or both ends.

In some embodiments, the larger diameter portions of the prosthetic devices can have an average or maximum diameter, for example, about or at least about 5%, 10%, 15%, 20%, 25%, 30%, 35%, 40%, 45%, 50%, 60%, 70%, 80%, 90%, 100%, or more relative to the average or maximum diameter of the smaller diameter portions, or ranges including any two of the foregoing values.

Disclosed herein are embodiments of methods to use pre-operative measurements of the uveolymphatic features such as diameter, length, tension, modulus, etc. to customize the SES 401 device to adequately provide tension and thus patency across the channel or canal, which in turn provides the required IOP reduction. Finite-element analysis (FEA) and modeling may be used to determine the patient anatomical sizing of the SES device 401 including features such as coil diameter, overall tube/device diameter, pitch, variance in pitch, entry and exit dimensions, etc.

Figure 16A:
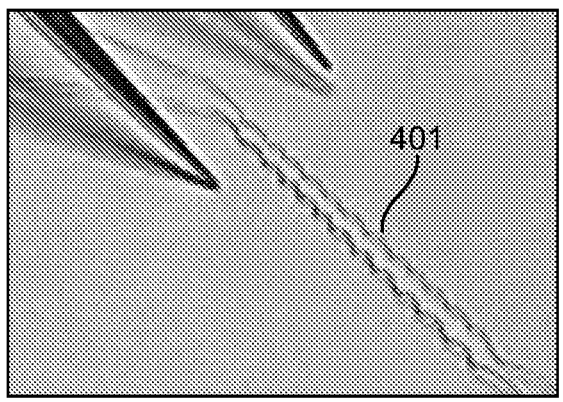
FIG. 16A are photographic images of the SES device made with shape-memory alloys and polymeric materials.
Figure 16B:
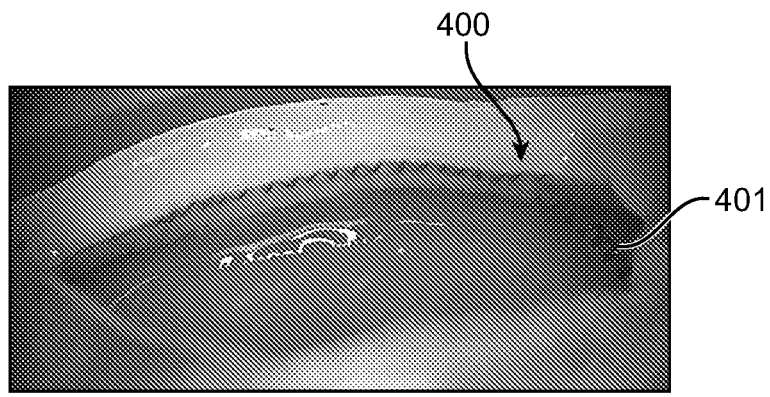
FIGS. 16B and 16C are photographic images of the SES device in-situ in the uveolymphatic vessel adequately dilated.
Figure 16C:
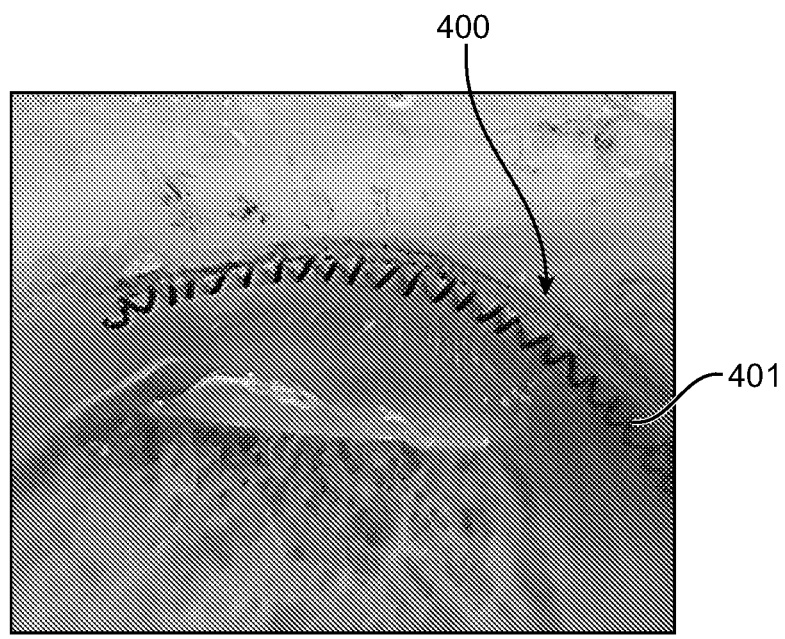

In some embodiments the SES device 401 may be directly implanted and slid into the uveolymphatic canal. FIG. 16A illustrates variants of the SES device made with shape-memory alloys and polymeric materials. FIGS. 16B and 16C shows the SES device 401 in-situ in the uveolymphatic vessel 400, adequately dilating the canal/vessel. Variants shown FIG. 16A may be utilized depending on the required dilation of the canal/vessel.

Figure 17:
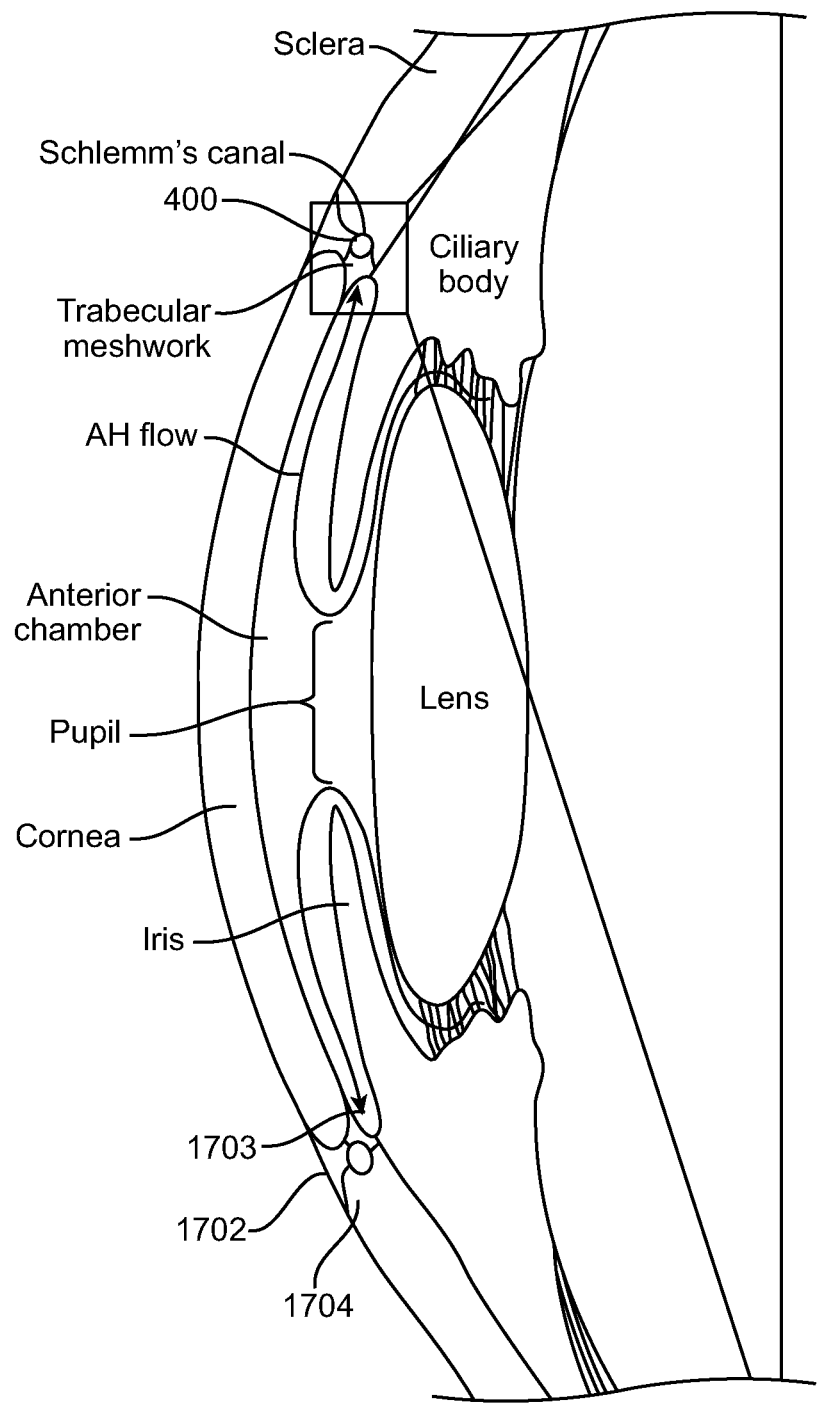
FIG. 17 illustrates a cross-sectional view of the eye, with indications for various locations of possible insertion of the SES device into the uveolymphatic vessel.

In some embodiments the SES device 401 may be delivered into the uveolymphatic canal/Schlemm's canal from the angle in the anterior chamber 1703, or outside the eye in the sub-conjunctival region, or the limbus region 1702 or the scleral region 1704. FIG. 17 illustrates a cross-sectional view of the eye, with indications for various locations of possible insertion of the SES device to access the uveolymphatic vessel/Schlemm's canal. One location shown is from the angle 1703 inside the anterior chamber of the eye. Other locations outside the eye, such as the limbus region 1702 or the sclera 1704 may be utilized to make an incision and access the uveolymphatic canal 400 directly below or underneath the scleral tissue. The access may be made easier by selective staining or dying of the canal. Such an access may provide additional benefits in safety and ease of delivery. Additionally, the corneal region may also be used as a location for first incision.

Disclosed herein are embodiments of methods to advance, deliver, position, re-position, and/or retrieve the prosthetic devices, such as SES 401 in a minimally invasive form. Temperature of the SES 401 can be manipulated (e.g., increased or decreased) by an insertion tool whose temperature can be externally controlled through an energy source (electrical, mechanical, thermal, RF, ultrasonic, etc.), such that it can alter the shape (shrink or expand) of the SES 401 to make insertion or retrieval procedures both minimally invasive, responsive, and easy to manipulate/handle. In some embodiments, the device can be repositioned by at least initially torqueing (e.g., twisting) the device rather than axially pushing or pulling the device in a proximal or distal direction.

Disclosed in FIGS. 18A-18C are embodiments of methods to advance, deliver, position, re-position, and/or retrieve the prosthetic devices, such as SES 401 in a minimally invasive form. In some embodiments, delivery device 1800 may contain an outer cannula 1801 to access the uveolymphatic vessel 400. The outer cannula 1801 may be made of metals, alloys, ceramics, or polymeric materials to access the canal. In some embodiments the outer cannula 1801 may have sharp leading edges to provide an incision to access the vessel 400. In some embodiments, the outer cannula 1801 may house an inner cannula 1802 or the SES device 401. In some embodiments the inner cannula 1802 may house the SES device and the inner cannula may be made of metals, alloys, ceramics, or polymeric materials. FIG. 18 illustrates a variant of an SES delivery device 1800 containing an outer cannula 1801 that houses an inner cannula 1802 that in turn houses the SES device 401. Sliders 1803 and 1804 to move the cannulas and the device are highlighted. The radius of the outer cannula 1801 and inner cannula 1802 may match that of the eye and canal 400 to allow adequacy in turn and advancement.

Figure 19A:
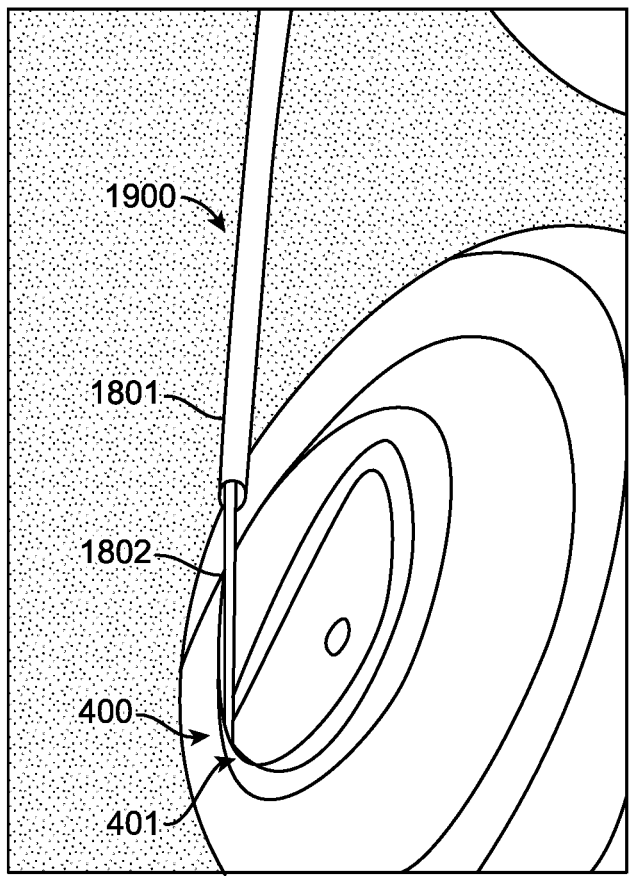
FIGS. 19A-19C illustrate a variant of an SES delivery device in-situ accessing the uveolymphatic vessel using the inner and outer cannula. The SES device delivery from the inner cannula is also shown.
Figure 19B:
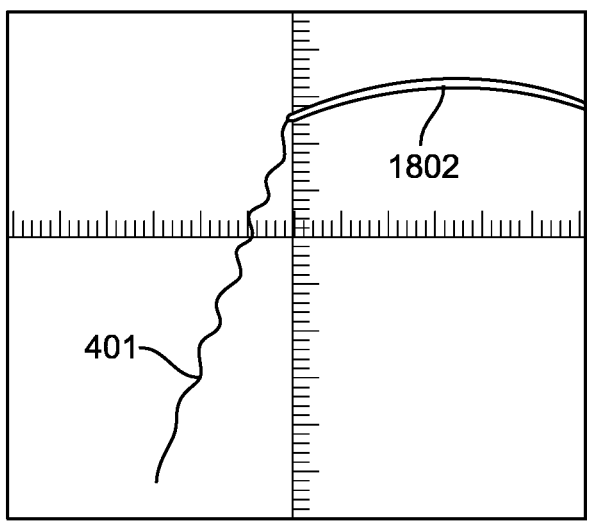
Figure 19C:
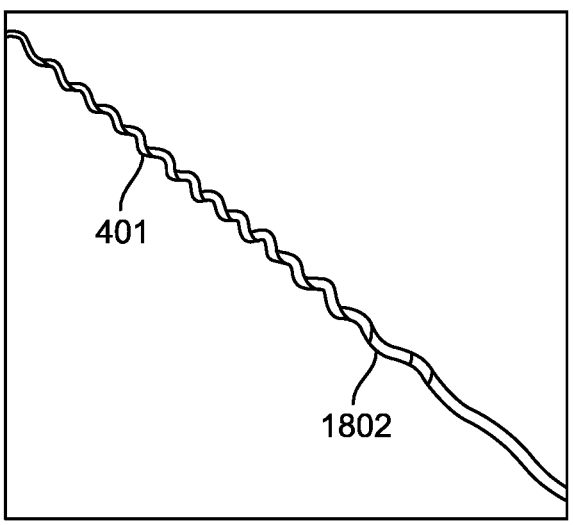

Disclosed herein are embodiments of methods to advance, deliver, position, re-position, and/or retrieve the prosthetic devices, such as SES 401 in a minimally invasive form. In some embodiments, delivery device 2000 may contain an outer cannula 1801 to access the uveolymphatic vessel 400. FIGS. 19A-19C illustrate a variant of an SES delivery device 2000 in-situ accessing the uveolymphatic vessel 400 using the outer cannula 1801 and delivering the SES device 401 using the inner cannula 1802. The SES device delivering the SES device 401 from the inner cannula 1802 is also shown.

Figure 20:
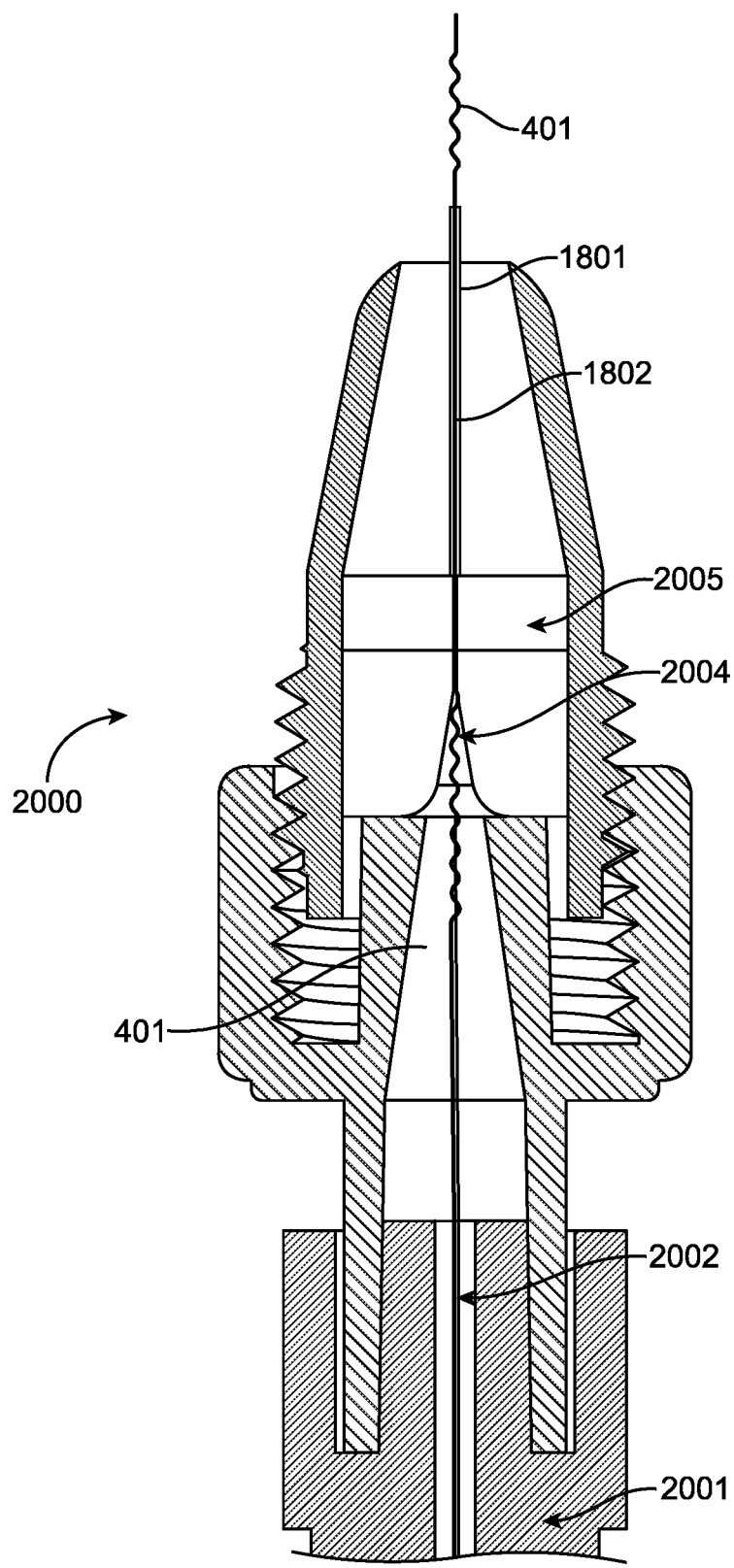
FIG. 20 illustrates a variant of an SES delivery device that utilizes a positive pressure system to control the advancement, deployment, and retraction of the SES device.

Disclosed herein are embodiments of methods to advance, deliver, position, re-position, and/or retrieve the prosthetic devices, such as SES 401 in a minimally invasive form. In some embodiments, delivery device 2000 may contain an outer cannula 1801 to access the uveolymphatic vessel 400. FIG. 20 illustrates a variant of an SES delivery device 2000 that utilizes a positive pressure system 2001 to control the advancement, deployment, and retraction of the SES device 401. In some embodiments, the delivery device 2000 may contain a plunger 2002 to control (increase or decrease the pressure) in the sealed chamber 2001 to control the movement of the SES device 401 further along the cannulas 1802 and 1801 into the uveolymphatic vessel 400. In some embodiments the delivery device 2000 may contain a channel with reducing perimeter, such as a cone 2004 to compress the SES device 401 into a smaller diameter into the inner 1802 or outer 1801 cannula or both. In some embodiments the delivery device 2000 may contain a sealed region 2005 (metal, alloys, ceramic, polymeric, silicone, foam, etc.) to provide a high-efficiency conversion of pressure differential from the chamber 2001 to linear movement of the SES device 401. In some embodiments the 2001 chamber may be liquid, gas, or air filled to create a pressure-controlled device. The device may be additionally powered by external energy sources. In some embodiments, the delivery system 2000 may be a provided as a unit to mate with existing syringes or delivery devices for ease of use.

Figure 21:
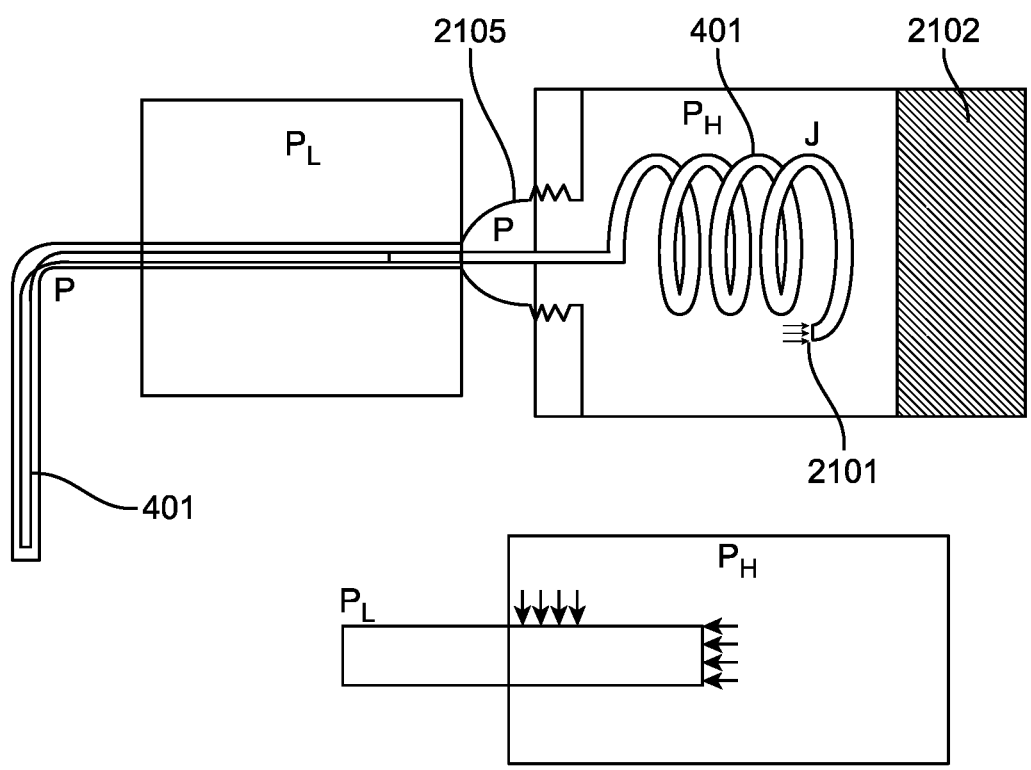
FIG. 21 illustrates a variant of an SES delivery device that utilizes a positive pressure system to control the advancement, deployment, and retraction of the SES device.

Disclosed herein are embodiments of methods to advance, deliver, position, re-position, and/or retrieve the prosthetic devices, such as SES 401 in a minimally invasive form. In some embodiments, delivery device 2000 may contain an outer cannula 1801 to access the uveolymphatic vessel 400. FIG. 21 illustrates a variant of an SES delivery device 2000 that utilizes a positive pressure system to control the advancement, deployment, and retraction of the SES device 401. In some embodiments the delivery device 2000 may contain a sealed region 2105 (metal, alloys, ceramic, polymeric, silicone, foam, etc.) to provide a high-efficiency conversion of pressure differential from the chamber 2101 to linear movement of the SES device 401. In some embodiments the 2101 chamber may be liquid, gas, or air filled to create a pressure-controlled device. The device may be additionally powered by external energy sources. In some embodiments the 2000 device may have a plunger or slider 2102 to control the delivery.

Figure 22A:
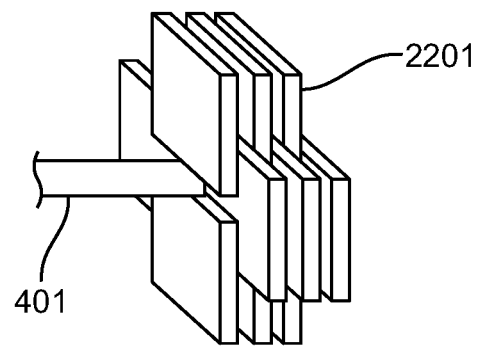
FIGS. 22A and 22B illustrate a variant of an SES delivery device that utilizes a multiple contact system similar to a feather-board to control the advancement, deployment, and retraction of the SES device.
Figure 22B:
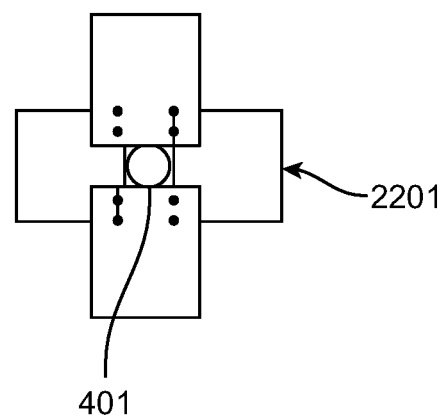

Disclosed herein are embodiments of methods to advance, deliver, position, re-position, and/or retrieve the prosthetic devices, such as SES 401 in a minimally invasive form. In some embodiments the delivery device may utilize various contact boards 2201 (or plates or feather-boards) that may contact the SES device 401 at a point, area or plane such that it can incrementally advance or retreat the device in any direction. In some embodiments, these contact boards 2201 may be made of metal, alloys, ceramic, polymeric, silicone materials. FIGS. 22A and 22B illustrate representative sketches of such as setup to control movement of the SES device 401.

Figure 23A:
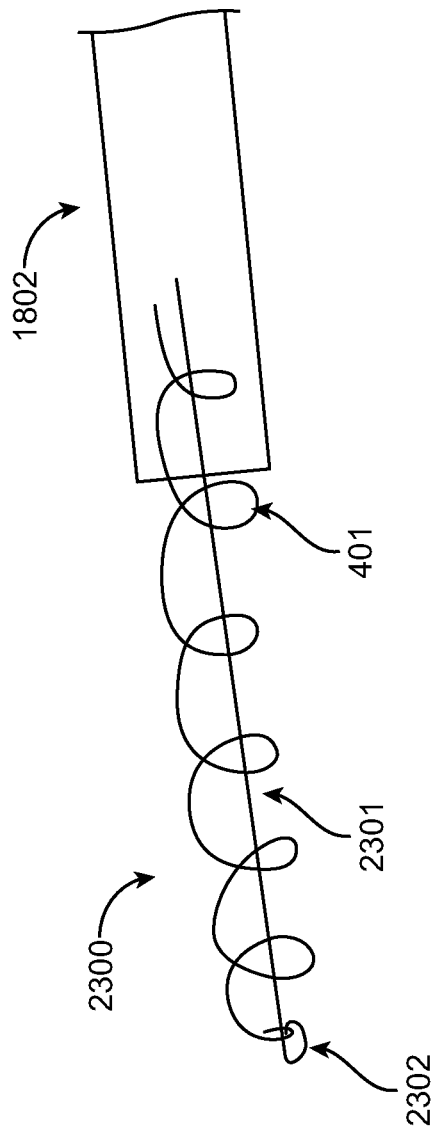
FIGS. 23A and 23B illustrate a variant of an SES delivery device that utilizes a lead guidewire that can selectively attach/detach to the SES device to control the advancement, deployment, and retraction of the SES device.
Figure 23B:
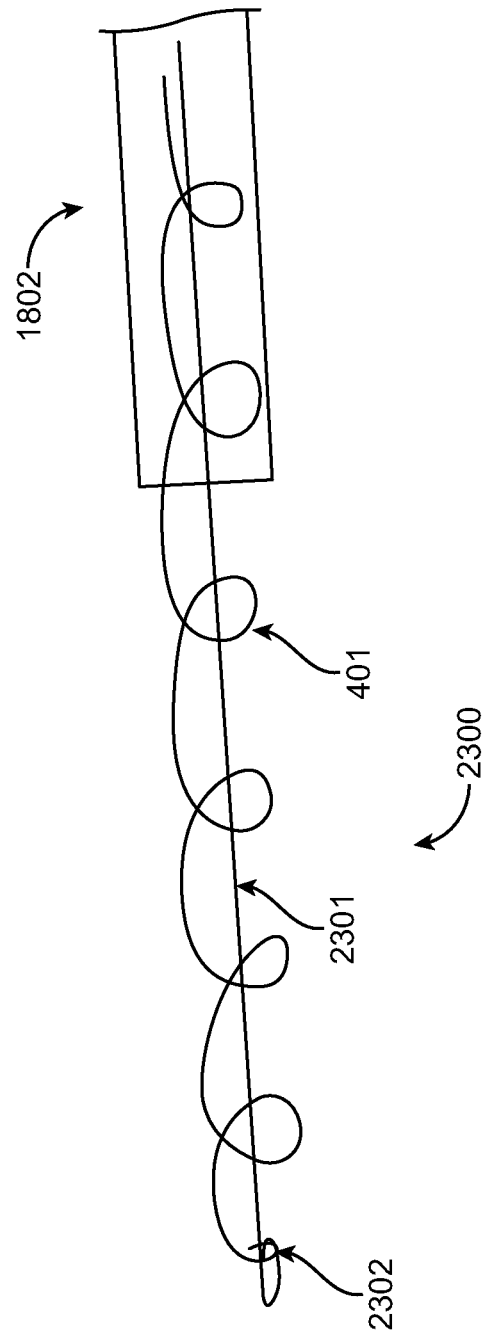

Disclosed herein are embodiments of methods to advance, deliver, position, re-position, and/or retrieve the prosthetic devices, such as SES 401 in a minimally invasive form. In some embodiments, the SES 401 device may have a leading guidewire 2301 that may lead the SES 401 device into the canal 400. In some embodiments, the guidewire 2301 may selectively attach to the SES device 401 with a mating portion 2302 by an external control through a trigger or movement. In some embodiments, the guidewire 2301 may stretch the SES device 401 into a smaller outer diameter to allow easier movement within the inner or outer cannula of the delivery system within or into the canal 400. In some embodiments the guidewire 2301 may be used to detach from or attach-to the SES device 401 using the mating portion 2302 that may be externally controlled trigger movement. FIGS. 23 and 23B illustrate a variant of an SES delivery device 2300 that utilizes a lead guidewire that can selectively attach/detach 2302 to the SES device to control the advancement, deployment, and retraction of the SES device 401.

Figure 24A:
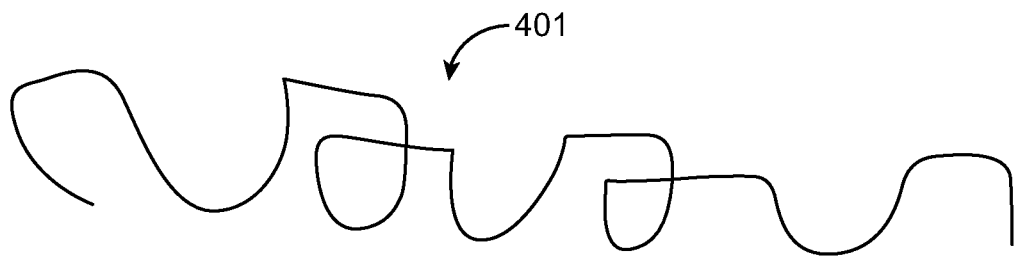
FIGS. 24A-24C illustrate a variant of an SES device and delivery system that utilizes a guide-wire to control the advancement, deployment, and retraction of the SES device.
Figure 24B:
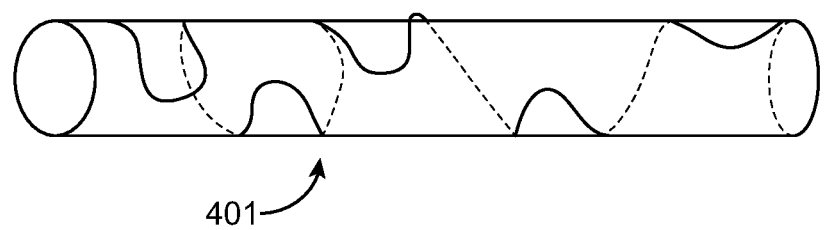
Figure 24C:
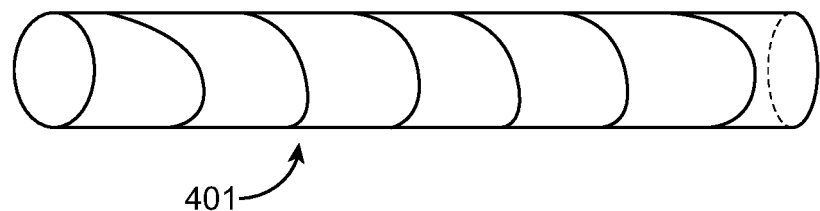

Disclosed herein are variants of the SES device 401 in a wire form that may be developed in non-helical forms with partial or semi-circular sweeps. In some other embodiments the SES device 401 in the wire form may have sweeps, turns either complete or partial to adequately stent the longitudinal section of the canal 400. FIGS. 24A-24C contain illustrations and examples of some such embodiments.

Figure 25A:
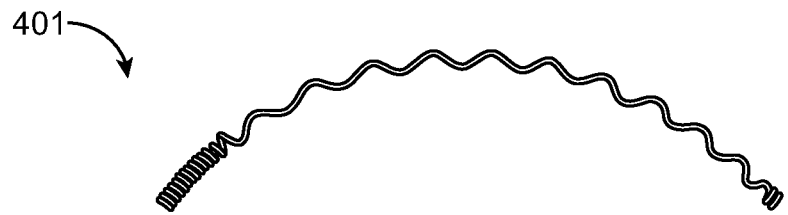
FIG. 25A illustrates a variant of a curved and electropolished SES device with wide pitch along the length of the device and a tighter finished closed loop ends.
Figure 25B:
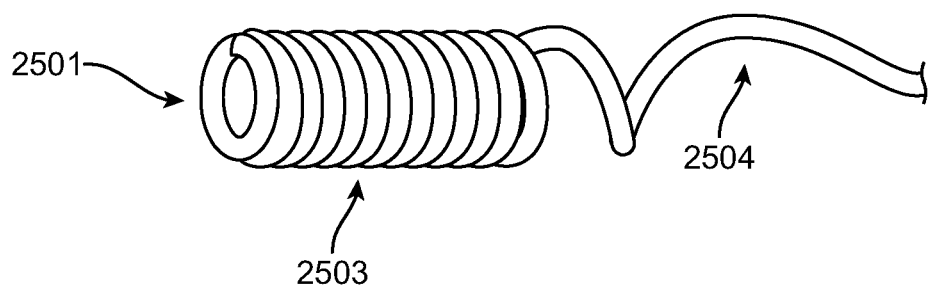
FIGS. 25B and 25C illustrate closer view of the proximal and distal end, respectively.
Figure 25C:
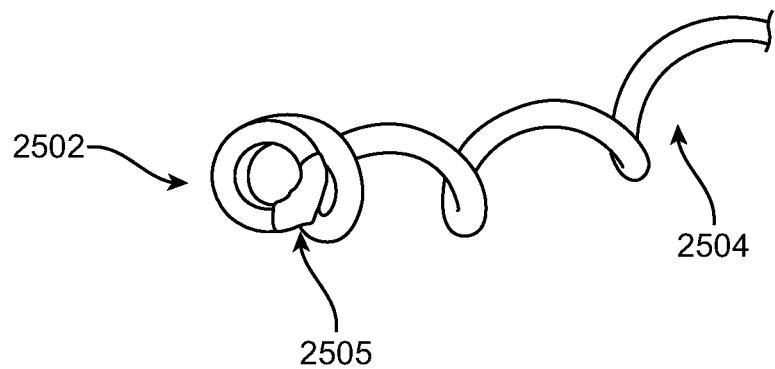

FIGS. 25A-25C illustrate a curved and electropolished SES device 401 formed from a single-stranded, helical, nickel-titanium or other metal wire. The SES device 401 of FIG. 25A displays a variable pitch along the length of the device and finished closed loop ends as illustrated in FIGS. 25B and 25C. In preferred embodiments, the radius of curvature for the SES device 401 may be designed to closely or exactly match the curvature of the uveolymphatic canal perimeter in the globe, so that no forces are applied which could deform the canal. In addition to having a conforming shape, it is preferred that the SES 401 be highly flexible with a very low bending stiffness so that no significant deforming forces will be transmitted to the canal even if there is a mismatch between the shape of the SES device and the shape of the canal and channel. In some less preferred embodiments, however, the radius of curvature and stiffness properties of the SES device may also be designed to provide some tension or additional expansion to improve the drainage through the collector channels.

In preferred embodiments, the SES device 401 will display a combination of (1) a very high flexibility, (2) a sufficient column strength to allow self-insertion, and (3) a sufficient hoop strength or crush resistance to maintain patency of the canal or channel. More specifically, the SES device 401 will preferably have very low bending stiffness along its length and so that it has minimal or no ability to deform the curvature of the Schlemm's Canal or the uveolymphatic canal perimeter. In such instances, the width, diameter, or cross-section of the coiled or otherwise bent wire in the main body 2504 will be sufficient to open and/or support the walls of the uveolymphatic canal to promote drainage of uveolymphatic fluid through the collector channels 2603, as described below.

While the helical monofilament SES device 401 of the present invention will have a very low bending stiffness and high flexibility, they will preferably also have sufficient column strength so that they may be inserted into and advanced through at least a portion of the Schlemm's canal without the use of a supporting mechanism or other deployment structure during implantation.

Additionally, the helical turns or other bends of the SES device 401 will typically be configured to open and/or support the walls of the Schlemm's Canal or the uveolymphatic canal perimeter after the SES device is implanted therein so that fluid may flow through the main channel of the Schlemm's Canal or the uveolymphatic canal into the surrounding collector channels.

FIGS. 25B and 25C illustrate closer view of the proximal and distal end, respectively. In some embodiments, the proximal end 2501 and/or distal end 2502 of the SES may have tighter, often but not necessarily closed, pitch 2503 in comparison to the main body 2504 of the device to allow smoother travel across the channel during delivery and additionally act as a by-pass into the aqueous chamber for improved circulation and drainage of fluid. The main body of the SES device 401 may have wider pitch 2504 to balance the least amount of material required to keep the uveolymphatic channel dilated for aqueous patency. In some embodiments, the SES may be processed via polishing methods such as mechanical, chemical, electrochemical polishing methods to improve the finish of the surface(s) as well as improve the biocompatibility of the surface(s). In some embodiments, the ends of the SES may be welded or otherwise rounded using LASER, heat, microwave, or other energy sources to form a closed loop 2505 or other desired shape for ease of travel and safer implantation, as shown in FIG. 25C.

Figure 26A:
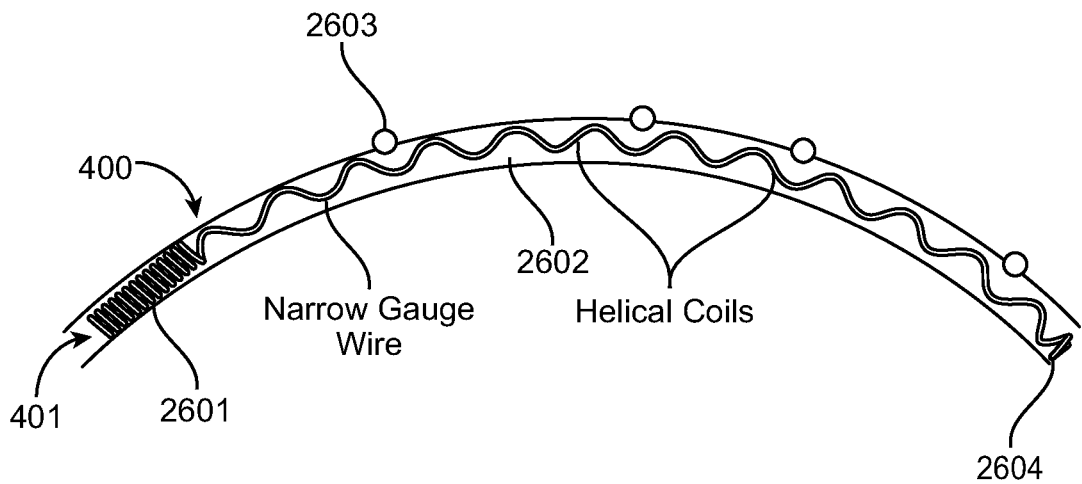
FIG. 26A illustrates a variant of a curved and electropolished SES device in situ in the uveolymphatic canal.
Figure 26B:
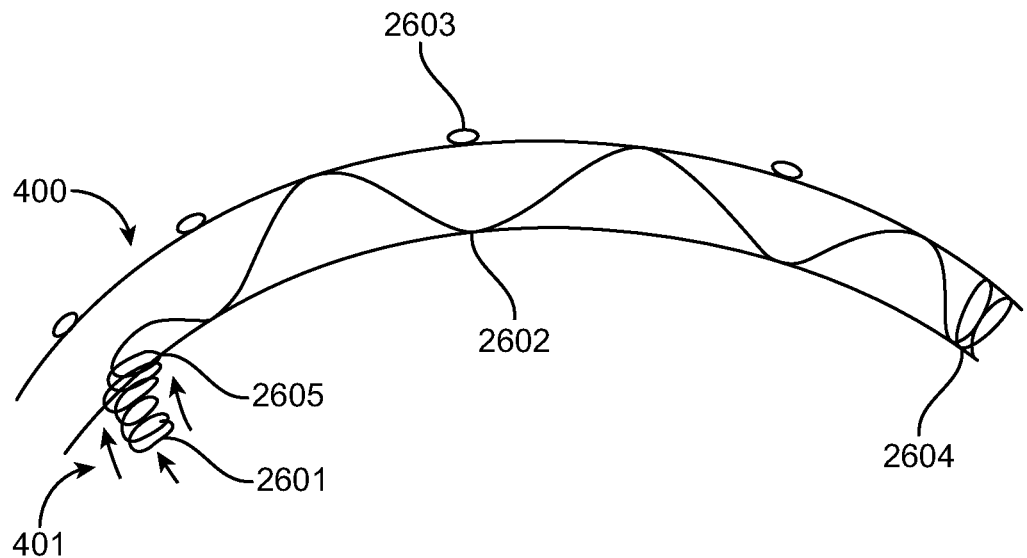
FIG. 26B illustrates a variant of a curved and electropolished SES device in situ in the uveolymphatic canal with the proximal end extended across the channel into the anterior chamber to create by-pass for fluid flow.
Figure 26C:
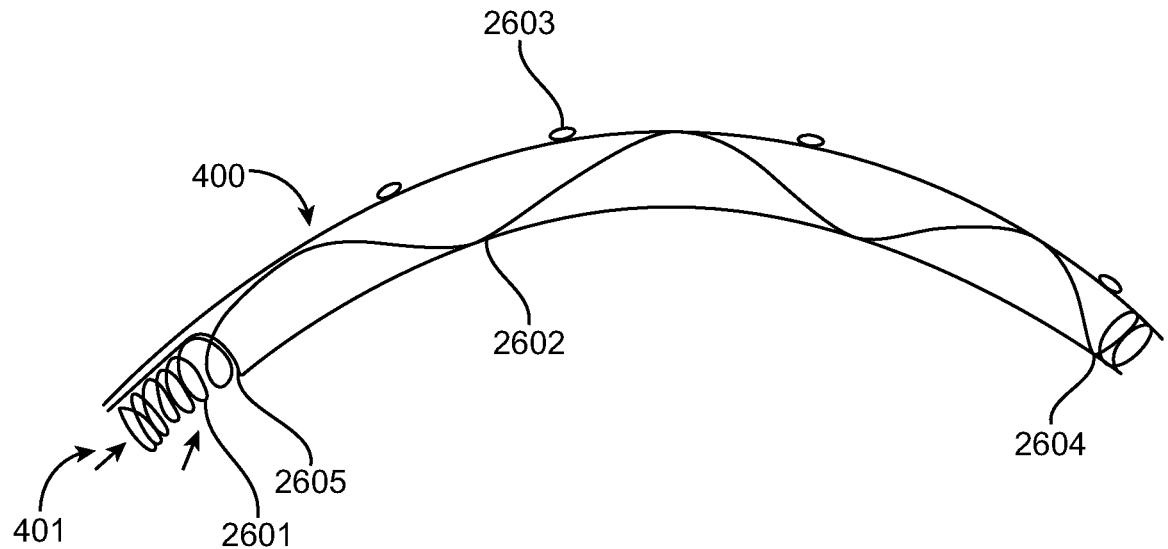
Figure 26D:
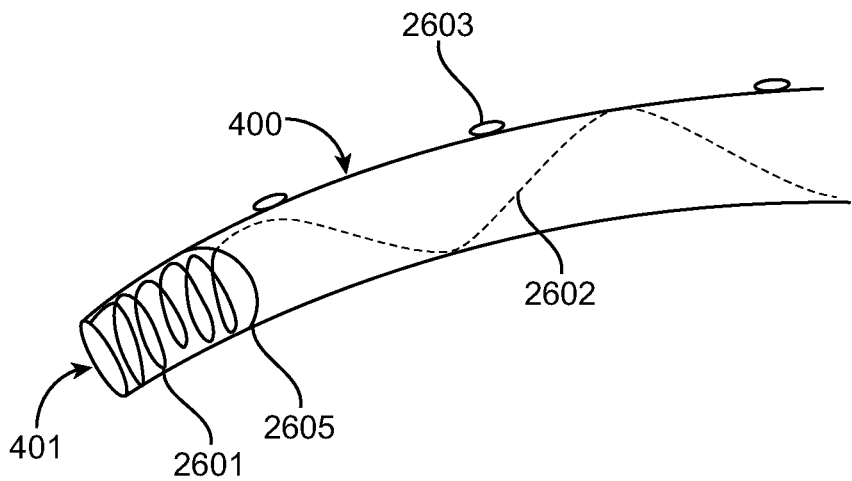
FIG. 26D contains a perspective closer view of the proximal end by-pass variant.
Figures 1, 26C:
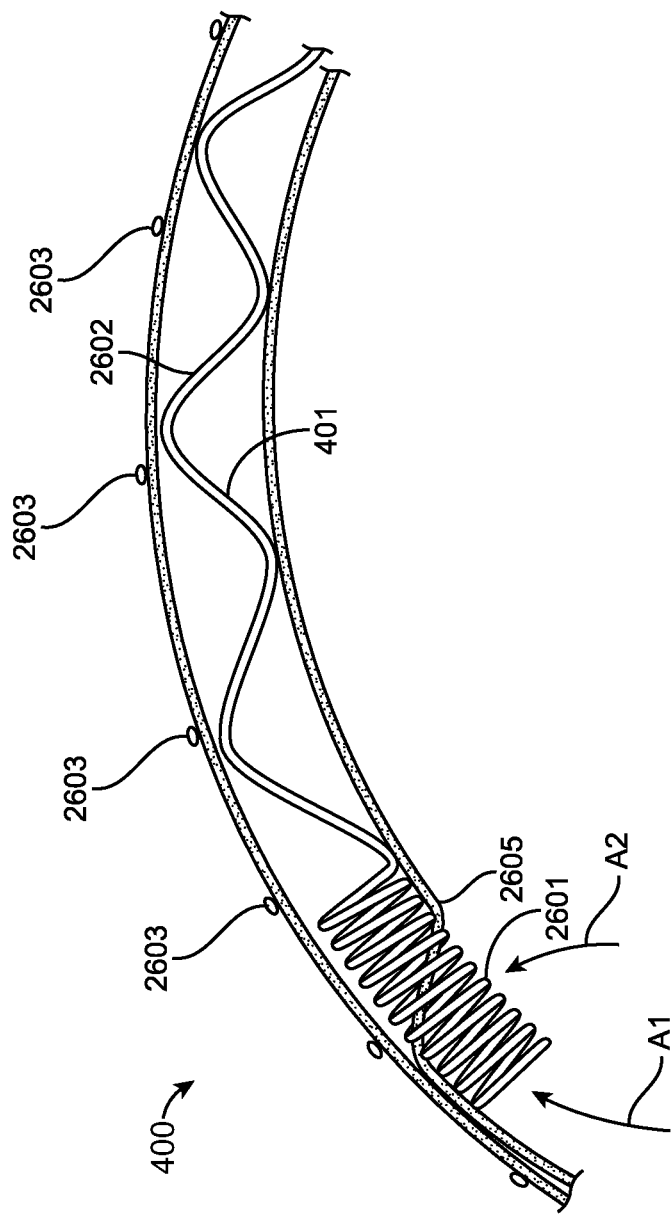

Disclosed herein are variants of the SES device in situ. FIG. 26A illustrates a variant of a curved and electropolished SES device 401 in situ in the uveolymphatic canal 400. The narrow-gauge wire of the 401 device prevents it from blocking the collector channels 2603 across the perimeter of the canal 400. In some embodiments, the SES device 401 may have even pitch across the length of the device. In some other embodiments as shown in FIG. 26A the SES device 401 may have tightly wound pitch towards the two ends 2601 and 2604 and wider pitch towards the main body 2602. The wider pitch 2602 on the main body can provide adequate patency of fluid within the channel without blocking any of the collector channels. The tightly wound ends can provide a complete or partial by-pass of fluid from the anterior chamber into the channel for aid fluid flow, clearance and reduce intraocular pressure. In some embodiments (as shown in FIG. 26B) the SES device 401 may reside in situ in the uveolymphatic canal 400 to dilate the canal with the proximal end 2601 extended across the channel at the wound 2605 into the anterior chamber to create by-pass for fluid flow. In similar embodiments, the wound 2605 and the proximal end 2601 can provide uninterrupted aqueous flow and clearance into the dilated uveolymphatic channel 400 to reduce intraocular pressure. In some embodiments, such a by-pass may be provided at both ends of the device. In some embodiments, (as shown in FIG. 26C) the SES device 401 may reside in situ in the uveolymphatic canal 400 to dilate the canal while with the proximal end 2601 extends along the same plane as the channel to create a partially collapsed wound opening 2605, i.e., the canal to the left of the wound opening in FIG. 26C is collapsed by the coil, and by-pass for fluid flow. In some embodiments, such a by-pass may be provided at both ends of the device. FIG. 26D contains a perspective closer view of the proximal end by-pass variant where the tightly wound proximal and/or distal end 2061 can be seen residing outside the canal 400 with access into the canal 400 at the wound 2605. The wider main body of the narrow gauge wire 2602 is shown to not block the collector channels 2603.

Figure 1:
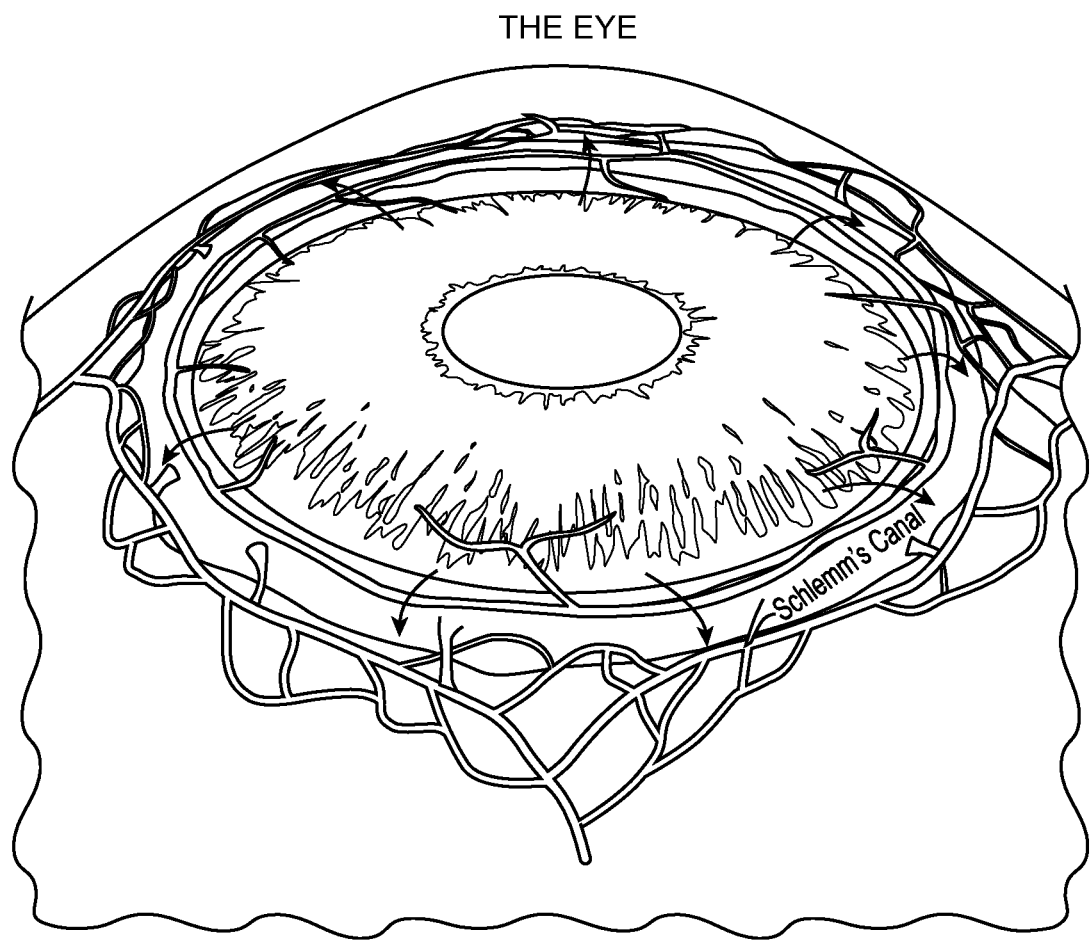
FIG. 1 illustrates an isometric sketch of the eye with a label indicating the location of the Schlemm's canal or the uveolymphatic vessel.
Figure 2:
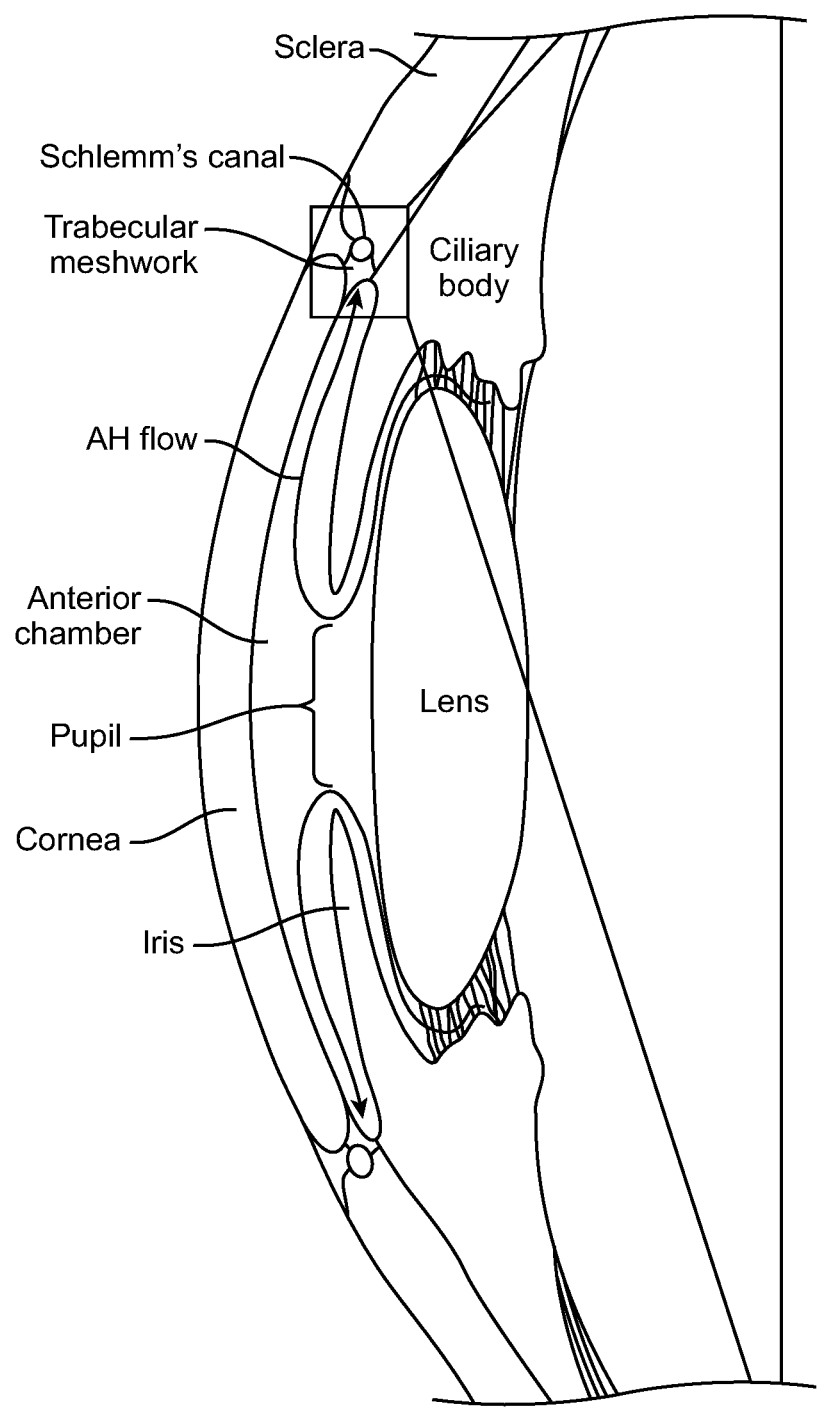
FIG. 2 illustrates a cross-sectional sketch of the eye with labels indicating aqueous humor flow from the posterior chamber ciliary body to the trabecular meshwork and into the Schlemm's canal.

As shown in FIG. 26C-1, in some instances, the coil at proximal end 2605 of the SES 400 which is positioned through the wound 2605, as shown in FIG. 26C, may have an open pitch that permits both axial flow through an open end of the coil in the direction of arrow A1 and lateral flow into the coil through exposed openings between adjacent turns of the coil in the direction of arrow A2. This is a particular advantage as it enhances fluid flow into the canal 400 which has been opened by the SES 401.

Figure 27:
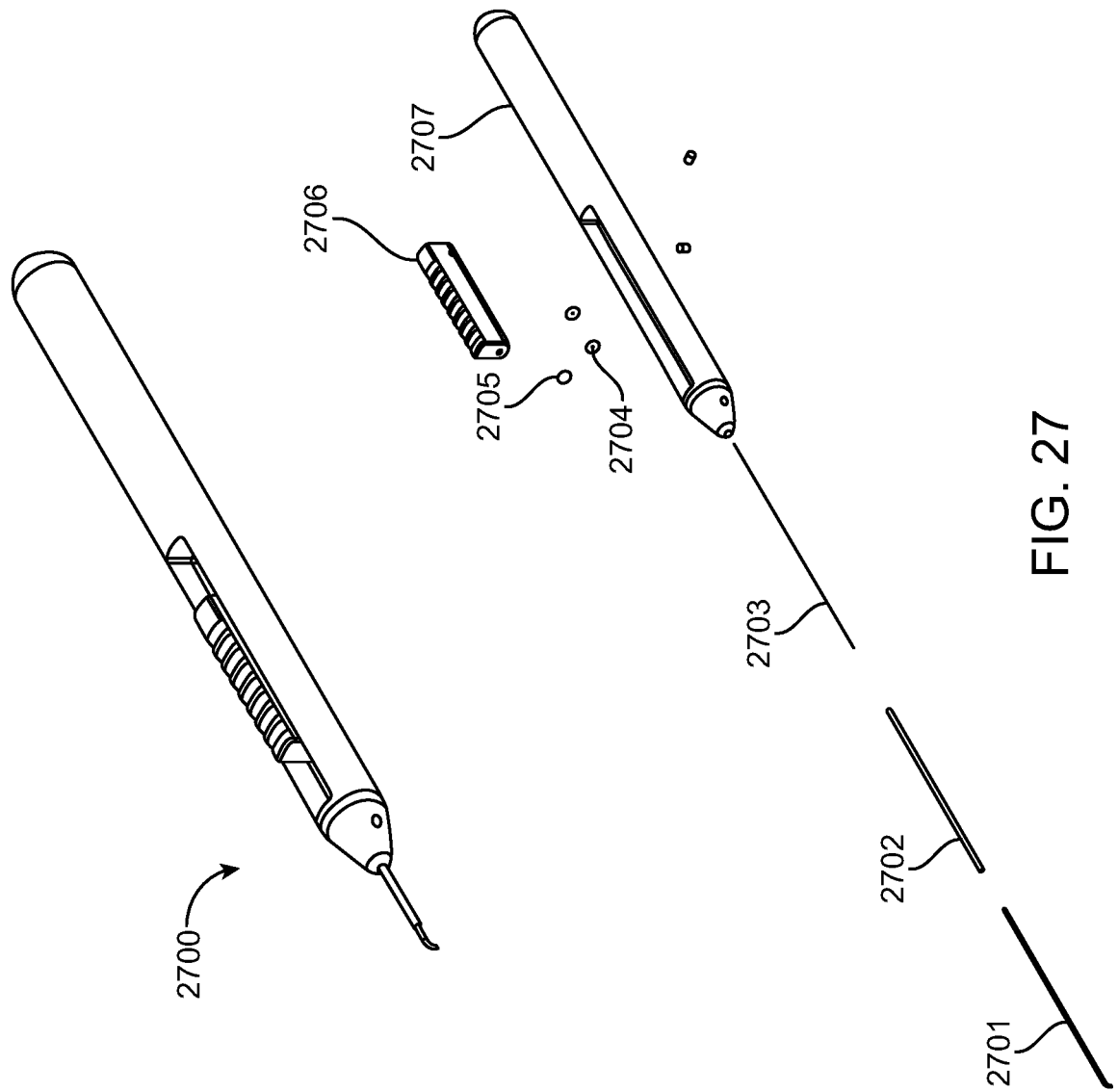
FIG. 27 illustrates a variant of a slide-inserted device to deploy the SES and a detailed exploded view of such a delivery system.

Disclosed herein are variants to deploy the SES device. FIG. 27 illustrates a variant of a slide-inserted device to deploy the SES and a detailed exploded view of such a delivery system. In some embodiments, the SES delivery system may use a sliding action delivery system. In some embodiments, the delivery device may comprise of a body 2707, set screws 2704, 2705 to control position of the outer or inner cannula 2701. In some embodiments a plunger made of a wire or braided wire 2702 may be used to deploy, delivery or retrieve the SES device. In some embodiments, the plunger 2702 may be controlled using a sliding wire 2703 which may be controlled using a slider 2706 resting within the inserter body 2707.

Disclosed herein are embodiments of methods to deliver the prosthetic device such as SES 401. In some embodiments, fluid pressure with a sealed region may be used to deliver the device. In some other embodiments, featherboards or collet advancers may be used to deliver the device, such that horizontal compression may lead to vertical motion or vice versa. In some other embodiments, shape-memory setting of the SES device 401 may be employed to deliver the device is a wire and have it self-expanded in-situ in the canal 400. In some other embodiments, the delivery device may have an un-coiler channel to improve vector and reduce friction in delivery the SES device 401. In some other embodiments, the SES device 401 may be pre-tightened or wound-up and delivered in this state and may relax and uncoil or expand in-situ in the canal 400. In some embodiments, torsional or axial rollers may be used to deliver the SES device 400 within the cannulas of the delivery device an in-situ in the canal 400. In some embodiments, piezo-electric vibrations with micromotors and vibrations may be used to deliver the SES device.

Disclosed herein are embodiments of methods to use pre-operative measurements of the Schlemm's canal physiology to customize the device, e.g., SES for the specific requirement. Imaging techniques such as optical microscopy, ultrasonography, fluoroscopy, near infra-red imaging, CT-scan, measurement of CSA (cross-sectional area), diameter, can be utilized, such as in a pre-treatment procedure to determine and customize the SES 401 design to fit the specific physiological and anatomical need of the patient. One or a plurality of customized devices can then be manufactured and then implanted, e.g., in a separate procedure. However, the sizing procedure and implantation procedure can be combined into a single procedure in other embodiments.

It is contemplated that various combinations or sub combinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "inserting the SES proximate to the distal end of the Schlemm's canal" includes "instructing the inserting an SES proximate to the distal end of the Schlemm's canal." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A device for maintaining patency of a channel of an uveolymphatic region or a Schlemm's canal in a patient's eye, said device comprising:
    an expansion member consisting of a single elongated element for radial expansion of the channel when inserted into the channel, the single elongate element consisting essentially of a single pre-shaped metal or polymeric filament that is biased to assume a curved configuration through its entire length to match a radius of curvature of the channel,
    wherein the single elongated element is a shape memory alloy wire having a diameter in a range from 0.001 mm to 1 mm and formed into a cylindrical helix having a central region with a pitch between successive turns in a range from 0.001 mm to 10 mm and diameter in a range from 0.001 mm to 10 mm when unconstrained;
    wherein the expansion member in its curved configuration has (i) sufficient radial strength to withstand compressive stresses exerted by the channel and (ii) sufficient void space in its structure to minimize blockage of the blocking of collector channels in the channel, when the expansion member is implanted in the channel.

2. The device for maintaining patency of claim 1, wherein the single pre-shaped metal or polymeric filament is a pre-shaped metal wire.

3. The device for maintaining patency of claim 2, wherein the pre-shaped metal wire is a shape or heat memory alloy wire.

4. The device for maintaining patency of claim 3, wherein the shape or heat memory alloy wire is a nickel-titanium alloy wire.

5. The device for maintaining patency of claim 1, wherein the single pre-shaped metal or polymeric filament in its curved configuration is at least partially formed with repeating helical turns.

6. The device for maintaining patency of claim 1, wherein the single pre-shaped metal or polymeric filament in its curved configuration is at least partially formed with repeating serpentine loops.

7. The device for maintaining patency of claim 1, wherein the pre-shaped metal or polymeric filament assume the curved configuration when free from constraint to conform to the shape of the channel.

8. The device for maintaining patency of claim 1, wherein at least one end of the single elongated element has a geometry different than that of the remainder of the single elongated element.

9. The device for maintaining patency of claim 1, wherein both ends of the have a geometry different than that of a central region of the single elongated element.

10. The device for maintaining patency of claim 1, wherein at least one end of the single elongated element is formed into a helix having one or more of a tighter pitch or smaller diameter than those of the central region.

11. The device for maintaining patency of claim 10, wherein both ends of the single elongated element are formed into a helix having one or more of a tighter pitch or smaller diameter than those of the central region.

12. The device for maintaining patency of claim 11, wherein tighter pitch is in a range from 0.001 mm to 1 mm and the smaller diameter is in a range from 0.001 mm to 1 mm.

13. The device for maintaining patency of claim 10, wherein the shape or heat memory alloy wire is a nickel-titanium alloy wire.

14. The device for maintaining patency of claim 10, wherein the single pre-shaped metal or polymeric filament in its curved configuration is at least partially formed with repeating helical turns.

15. The device for maintaining patency of claim 10, wherein the pre-shaped metal or polymeric filament assume the curved configuration when free from constraint to conform to the shape of the channel.

16. The device for maintaining patency of claim 10, wherein the single elongated element has at least one end formed in a loop.

17. The device for maintaining patency of claim 10, wherein the single elongated element has sufficient flexibility and low bending stiffness, such that no substantial deforming forces are transmitted to the channel by the single elongated element when implanted in the channel.

18. The device for maintaining patency of claim 1, wherein the single elongated element has been polished via mechanical, chemical or electrochemical methods to improve finish and biocompatibility.

19. The device for maintaining patency of claim 1, wherein the single elongated element has at least one end formed in a loop.

20. The device for maintaining patency of claim 1, wherein the single elongated element has at least one end formed as a wound coil.

21. The device for maintaining patency of claim 20, wherein the coil at the at least one end is tightly wound.

22. The device for maintaining patency of claim 20, wherein the coil at the at least one end has sufficient strength space between adjacent turns to permit fluid flow therethrough.

23. The device for maintaining patency of claim 1, wherein the single elongated element comprises at least one feature at least one end thereof configured to facilitate manipulation.

24. The device for maintaining patency of claim 1, wherein the single elongated element is at least partially biodegradable or bioresorbable.

25. The device for maintaining patency of claim 1, wherein the single elongated element comprises a drug-eluting member formed on a surface thereof or embedded therein.

26. The device for maintaining patency of claim 1, wherein the single elongated element comprises a hydrophilic or hydrophobic coating to aid in the safety and efficacy of the device within the eye.

27. The device for maintaining patency of claim 1, wherein the single elongated element includes a by-pass feature configured to permit aqueous flow between Schlemm's canal and an anterior chamber of the eye.

28. The device for maintaining patency of claim 27, wherein the by-pass feature is located at an entry, an exit, or along a length of the device.

29. The device for maintaining patency of claim 1, wherein the single elongated element is formed at least partly form a polymeric material selected from a group consisting of polyvinylidene fluoride, polyvinylidene difluoride (PVDF), polyvinylpyrrolidone (PVP), polyurethane, polyethylene glycol (PEG), polylactic acid (PLA), polycaprolactone (PCL), polyglycolic acid (PGA), polymethylmethacrylate (PMMA), polyacrylates, polyamide, polyimide, polyesters, silicone, and carbon-composites.

30. The device for maintaining patency of claim 1, wherein the single elongated element is formed at least partly from a metal or metal alloy selected from a group consisting of titanium, stainless steel, cobalt-chrome alloy, gold, platinum, silver, iridium, tantalum, tungsten, aluminum, and vanadium.

31. The device for maintaining patency of claim 1, wherein the single elongated element has sufficient flexibility and low bending stiffness, such that no substantial deforming forces are transmitted to the channel by the single elongated element when implanted in the channel.

32. The device for maintaining patency of claim 1, wherein the single elongated element has a proximal end, wherein the single elongated element is configured to be pushed by a delivery cannula from the proximal end into an incision in the channel.

33. A device for maintaining patency of a channel of an uveolymphatic region or a Schlemm's canal in a patient's eye, said device comprising:
  an expansion member consisting of a single elongated element for radial expansion of the channel when inserted into the channel, the single elongate element consisting essentially of a single pre-shaped metal or polymeric filament that is biased to assume a curved configuration through its entire length to match a radius of curvature of the channel, wherein at least one end of the single elongated element is formed into a helix having one or more of a tighter pitch or smaller diameter than those of the central region, wherein the tighter pitch is in a range from 0.001 mm to 1 mm and the smaller diameter is in a range from 0.001 mm to 1 mm;
  wherein the expansion member in its curved configuration has (i) sufficient radial strength to withstand compressive stresses exerted by the channel and (ii) sufficient void space in its structure to minimize blockage of the blocking of collector channels in the channel, when the expansion member is implanted in the channel.

\* \* \* \* \*